(12) United States Patent
Naor

(10) Patent No.: US 10,149,759 B2
(45) Date of Patent: Dec. 11, 2018

(54) HEART VALVE ASSISTIVE PROSTHESIS

(71) Applicant: Mitrassist Medical Ltd., Caesarea (IL)

(72) Inventor: Gil Naor, Hofit (IL)

(73) Assignee: Mitrassist Medical Ltd., Caesarea (IL)

( * ) Notice: Subject to any disclaimer, the term of this patent is extended or adjusted under 35 U.S.C. 154(b) by 423 days.

(21) Appl. No.: 14/889,158

(22) PCT Filed: May 8, 2014

(86) PCT No.: PCT/IL2014/050414
§ 371 (c)(1),
(2) Date: Nov. 5, 2015

(87) PCT Pub. No.: WO2014/181336
PCT Pub. Date: Nov. 13, 2014

(65) Prior Publication Data
US 2016/0074164 A1 Mar. 17, 2016

Related U.S. Application Data

(60) Provisional application No. 61/910,386, filed on Dec. 1, 2013, provisional application No. 61/821,317, filed on May 9, 2013.

(51) Int. Cl.
*A61F 2/24* (2006.01)
(52) U.S. Cl.
CPC ............ *A61F 2/2436* (2013.01); *A61F 2/246* (2013.01); *A61F 2/2409* (2013.01);
(Continued)

(58) Field of Classification Search
CPC .... A61F 2/2427; A61F 2/2412; A61F 2/2409; A61F 2/2403; A61F 2250/0059; A61F 2250/0031
See application file for complete search history.

(56) References Cited

U.S. PATENT DOCUMENTS 7,381,220 B2 6/2008 Macoviak et al.
8,092,520 B2 1/2012 Quadri
(Continued)

FOREIGN PATENT DOCUMENTS

CA 2840084 12/2012
WO WO 2004/030568 4/2004
(Continued)

OTHER PUBLICATIONS

Supplementary European Search Report and the European Search Opinion dated Dec. 13, 2016 From the European Patent Office Re. Application No. 14794056.3. (8 Pages).
(Continued)

*Primary Examiner* — Julie A Szpira

(57) ABSTRACT

A device for placing in a cardiac valve to assist operation of natural cardiac valve leaflets, the device including a frame for anchoring the device, configured to be placed upstream of the cardiac annulus and shaped to prevent the frame from shifting downstream of the cardiac valve annulus, and at least one anchor extension attached to the frame, the anchor extension configured to extend through the leaflets of the cardiac valve at commissures of the cardiac valve and behind the natural leaflets, preventing the anchor extensions from shifting back from the downstream side of the annulus to the upstream side of the annulus. Related apparatus and methods are also described.

21 Claims, 27 Drawing Sheets

(52) U.S. Cl.
CPC .... *A61F 2/2418* (2013.01); *A61F 2220/0008* (2013.01); *A61F 2230/0071* (2013.01); *A61F 2250/007* (2013.01); *A61F 2250/0039* (2013.01)

(56) References Cited

U.S. PATENT DOCUMENTS

| | | | |
|---|---|---|---|
| 2001/0010017 | A1 | 7/2001 | Letac et al. |
| 2003/0199975 | A1 | 10/2003 | Gabbay |
| 2004/0127981 | A1 | 7/2004 | Rahdert et al. |
| 2005/0261765 | A1 | 11/2005 | Liddicoat |
| 2006/0058871 | A1 | 3/2006 | Zakay et al. |
| 2007/0156233 | A1 | 7/2007 | Kapadia et al. |
| 2007/0185571 | A1 | 8/2007 | Kapadia et al. |
| 2007/0270943 | A1 | 11/2007 | Solem et al. |
| 2008/0065204 | A1 | 3/2008 | Macoviak et al. |
| 2010/0280606 | A1* | 11/2010 | Naor ............ A61F 2/2418 623/2.18 |
| 2010/0298931 | A1 | 11/2010 | Quadri et al. |
| 2011/0137397 | A1 | 6/2011 | Chau et al. |
| 2011/0319990 | A1 | 12/2011 | Macoviak et al. |
| 2012/0078353 | A1 | 3/2012 | Quadri et al. |
| 2012/0215303 | A1 | 8/2012 | Quadri et al. |

FOREIGN PATENT DOCUMENTS

| | | |
|---|---|---|
| WO | WO 2004/089250 | 10/2004 |
| WO | WO 2005/027797 | 3/2005 |
| WO | WO 2010/106438 | 9/2010 |
| WO | WO 2011/137531 | 11/2011 |
| WO | WO 2012/103204 | 8/2012 |
| WO | WO 2013/037519 | 3/2013 |
| WO | WO 2014/181336 | 11/2014 |

OTHER PUBLICATIONS

Notification of Office Action dated Apr. 24, 2017 From the State Intellectual Property Office of the People's Republic of China Re. Application No. 201480039350.7 and Its Summary Into English. (16 Pages).

Translation of Notification of Office Action dated Sep. 2, 2016 From the State Intellectual Property Office of the People's Republic of China Re. Application No. 201480039350.7.

International Preliminary Report on Patentability dated Nov. 19, 2015 From the International Bureau of WIPO Re. Application No. PCT/IL2014/050414.

International Search Report and the Written Opinion dated Aug. 24, 2014 From the International Searching Authority Re. Application No. PCT/IL2014/050414.

\* cited by examiner

HEART VALVE ASSISTIVE PROSTHESIS

RELATED APPLICATIONS

This application is a National Phase of PCT Patent Application No. PCT/IL2014/050414, having International filing date of May 8, 2014, which claims the benefit of priority under 35 USC § 119(e) of U.S. Provisional Patent Application Nos. 61/821,317, filed on May 9, 2013 and 61/910,386, filed on Dec. 1, 2013.

The contents of the above applications are all incorporated by reference as if fully set forth herein in their entirety.

FIELD AND BACKGROUND OF THE INVENTION

The present invention, in some embodiments thereof, relates to a cardiac valve support, more particularly, but not exclusively, to an assistive prosthesis for a heart valve and, even more particularly, but not exclusively, to an assistive prosthesis for a mitral valve.

The mitral valve and tricuspid valve are unidirectional heart valves which separate the left and right atria respectively, from corresponding heart ventricles. These valves have a distinct anatomical and physiological structure, having two (mitral) or three (tricuspid) sail-like leaflets connected to a subvalvular mechanism of strings (chordae tendinae) and papillary muscles forming a part of the heart's ventricular shape, function and size.

The heart has four chambers: the right and left atria, and the right and left ventricles. The atria receive blood and then pump it into the ventricles, which then pump it out into the body.

Synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves which are supposed to ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

The opening and closing of heart valves occur primarily as a result of pressure differences. For example, the opening and closing of the mitral valve occurs as a result of the pressure differences between the left atrium and the left ventricle. During ventricular diastole, when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole, intraventricular pressure rises above the pressure in the atrium and pushes the mitral valve shut.

As noted above, these valves feature a plurality of leaflets connected to chordae tendinae and papillary muscles, which allow the leaflets to resist the high pressure developed during contractions (pumping) of the left and right ventricles. In a healthy heart, the chords become taut, preventing the leaflets from being forced into the left or right atria and inverted. Prolapse is a term used to describe a condition wherein coaptation edges of each leaflet initially may coapt and close, but then the leaflets rise higher, the edges separate, and the valve leaks. This is normally prevented by a contraction of the papillary muscles and by the normal length of the chords. Contraction of the papillary muscles is usually simultaneous with the contraction of the ventricle and serves to keep healthy valve leaflets tightly shut at peak contraction pressures exerted by the ventricle.

Valve malfunction can result from the chords becoming stretched, and in some cases tearing. When a chord tears, the result is a flailed leaflet. Also, a normally structured valve may not function properly because of an enlargement of the valve annulus pulling the leaflets apart. This condition is referred to as a dilation of the annulus and generally results from heart muscle failure. In addition, the valve may be defective at birth or because of an acquired disease, usually infectious or inflammatory.

Diseases of the valves can cause either narrowing (stenosis) or dilatation (regurgitation, insufficiency) of the valve, or a combination of those. Surgical treatment for repair or replacement of the valves typically includes an open-heart procedure, extracorporeal circulation and, if replaced, a complete or partial resection of the diseased valve.

Background Art Includes:

PCT Published Patent Application WO2011/137531 of Lane et al;

PCT Published Patent Application WO2010/106438 of Naor et al;

U.S. Published Patent Application 2010/010017 of Letac et al;

U.S. Published Patent Application 2007/0156233 of Kapadia et al;

U.S. Published Patent Application 2004/0127981A1 of Randert et al; and

U.S. Pat. No. 7,381,220 to Macoviak et al.

The disclosures of all references mentioned above and throughout the present specification, as well as the disclosures of all references mentioned in those references, are hereby incorporated herein by reference.

SUMMARY OF THE INVENTION

The present invention, in some embodiments thereof, relates to a support for an assistive prosthesis for a heart valve or to a support for a replacement heart valve.

The present invention, in some embodiments thereof, also relates to an assistive prosthesis for a heart valve.

In some embodiments, the assistive prosthesis is placed over a subject's natural heart valve, allowing movement of the natural heart valve leaflets. The subject's natural heart valve may be defective, allowing some blood to leak back through the natural heart valve during a heart beat cycle. However, the natural leaflets still block much of the blood from retrograding through the natural heart valve. By placing the assistive prosthesis over leaflets of the natural heart valve, the natural leaflets absorb much of the back pressure, and the assistive prosthesis blocks retrograde blood.

According to an aspect of some embodiments of the present invention there is provided a device for placing in a cardiac valve to assist operation of natural cardiac valve leaflets, the device including a frame for anchoring the device, configured to be placed upstream of the cardiac annulus and shaped to prevent the frame from shifting downstream of the cardiac valve annulus, and at least one anchor extension attached to the frame, the anchor extension configured to extend through the leaflets of the cardiac valve at commissures of the cardiac valve and behind the natural leaflets, preventing the anchor extensions from shifting back from the downstream side of the annulus to the upstream side of the annulus.

According to some embodiments of the invention, the anchor extension is configured so as not to interfere with movement of a natural cardiac leaflet.

According to some embodiments of the invention, the anchor extension is configured to extend through the leaflets of the cardiac valve at the commissures of the cardiac valve and beyond the natural leaflets and coming behind the natural leaflets.

According to some embodiments of the invention, the anchor extension is attached to the frame at a first location, extends behind the natural leaflet, and is attached back to the frame at a second location.

According to an aspect of some embodiments of the present invention there is provided a device for placing in a cardiac valve to assist operation of natural cardiac valve leaflets, the device including a frame for anchoring the device, configured to be placed upstream of the cardiac annulus and shaped to prevent the frame from shifting downstream of the cardiac valve annulus, a sheet of flexible material attached to the frame, configured to be placed within the annulus of the cardiac valve, defining a lumen of the sheet extending from an upstream side of the annulus to a downstream side of the annulus, and at least two posts attached to the frame, the posts configured to extend along the lumen of the sheet and prevent the lumen from collapsing back from the downstream side of the annulus to the upstream side of the annulus.

According to some embodiments of the invention, the posts are attached to each other at their downstream end. According to some embodiments of the invention, the at least two posts are exactly two posts.

According to some embodiments of the invention, the cardiac valve is a mitral valve and the posts are attached to the frame at an angle which directs a downstream side of the flexible sheet away from the Left Ventricle Outflow Track (LVOT).

According to some embodiments of the invention, the lumen defined by the sheet of flexible material extends 2-7 mm longer than a length of the natural cardiac valve leaflets.

According to some embodiments of the invention, the cardiac valve is a mitral valve and a side of the frame is configured to be at an angle which directs a downstream side of the flexible sheet away from the aortic valve so as not to interfere with the Left Ventricle Outflow Track (LVOT). According to some embodiments of the invention, the angle is in a range between 50 and 85 degrees.

According to some embodiments of the invention, each one of the posts is curved from a base attached to the frame to a commissure at a coaptation line of the natural cardiac leaflets.

According to some embodiments of the invention, the device further includes at least one anchor extension attached to the frame, the anchor extension configured to extend beyond the leaflets of the cardiac valve at commissures of the cardiac valve and back behind the leaflets of the cardiac valve, circumventing the natural leaflets preventing the anchor extensions from shifting back from the downstream side of the annulus to the upstream side of the annulus.

According to some embodiments of the invention, the anchor extension configured to extend beyond the leaflets of the cardiac valve at commissures of the cardiac valve and back behind the leaflets of the cardiac valve is configured so as not to interfere with movement of a natural cardiac leaflet.

According to some embodiments of the invention, the anchor extensions are attached to the posts.

According to some embodiments of the invention, further including at least a plurality of seal extensions attached to the frame, the seal extensions configured to attach a seal to an outside circumference of the device, for sealing between the sheet of flexible material and the cardiac valve.

According to some embodiments of the invention, further including a seal configured for sealing between the sheet of flexible material and the cardiac valve.

According to some embodiments of the invention, the sheet of flexible material is tubular shaped. According to some embodiments of the invention, the sheet of flexible material includes an asymmetrical shape similar to an asymmetrical shape of a natural cardiac valve.

According to some embodiments of the invention, at least part of the frame is shaped to form a D-shaped annulus.

According to some embodiments of the invention, the sheet of flexible material includes a plurality of flexible sheets connected to form a shape defining a lumen. According to some embodiments of the invention, the sheet of flexible material includes a plurality of leaflet-shaped flexible sheets connected to form a shape defining a lumen.

According to some embodiments of the invention, the leaflet-shaped flexible sheets include two leaflet-shaped flexible sheets. According to some embodiments of the invention, the two leaflet-shaped flexible sheets include a smaller leaflet-shaped sheet and a larger leaflet-shaped sheet.

According to some embodiments of the invention, the frame, at least when expanded, has a diameter greater than a diameter of the cardiac annulus.

According to an aspect of some embodiments of the present invention there is provided a device for placing in a cardiac valve to assist operation of the cardiac valve, the device including a frame for anchoring the device, configured to be placed upstream of the cardiac annulus and shaped to prevent the frame from shifting downstream of the cardiac valve annulus, a sheet of flexible material attached to the frame, configured to be placed within the annulus of the cardiac valve, defining a lumen of the sheet extending from an upstream side of the annulus to a downstream side of the annulus, and a plurality of anchor extensions attached to the frame, the anchor extensions configured to extend beyond the commissures of the natural cardiac valve and back behind the commissures of the natural cardiac valve, circumventing the commissures without interfering with movement of the natural leaflets, preventing the anchor extensions from shifting back from the downstream side of the annulus to the upstream side of the annulus.

According to some embodiments of the invention, the frame, at least when expanded, has a diameter greater than a diameter of the cardiac annulus.

According to some embodiments of the invention, further including at least a plurality of seal extensions attached to the frame, the seal extensions configured to attach a seal to an outside circumference of the device, for sealing between the sheet of flexible material and the cardiac valve.

According to some embodiments of the invention, further including a seal configured for sealing between the sheet of flexible material and the cardiac valve.

According to an aspect of some embodiments of the present invention there is provided a device for placing in a cardiac valve to assist operation of the cardiac valve, the device including a frame for anchoring the device, configured to be placed upstream of the cardiac annulus and shaped to prevent the frame from shifting downstream of the cardiac valve annulus, a sheet of flexible material attached to the frame, configured to be placed within the annulus of the cardiac valve, defining a lumen of the sheet extending from an upstream side of the annulus to a downstream side of the annulus, and at least one leaflet anchor extension attached to the frame, the leaflet anchor extension configured to extend beyond at least one leaflet of the cardiac valve and back behind the leaflet of the cardiac valve, circumventing the leaflet without interfering with movement of the leaflet, preventing the anchor extension from shifting back from the downstream side of the annulus to the upstream side of the annulus.

According to some embodiments of the invention, the cardiac valve is a mitral valve and the leaflet anchor extension is attached to the frame and is shaped to extend behind a leaflet of the mitral valve which is distant from the aortic valve.

According to some embodiments of the invention, further including at least a plurality of seal extensions attached to the frame, the seal extensions configured to attach a seal to an outside circumference of the device, for sealing between the sheet of flexible material and the cardiac valve.

According to some embodiments of the invention, further including a seal configured for sealing between the sheet of flexible material and the cardiac valve.

According to some embodiments of the invention, the frame, at least when expanded, has a diameter greater than a diameter of the cardiac annulus.

According to an aspect of some embodiments of the present invention there is provided a method of inserting a prosthesis for placing in a cardiac valve to assist operation of natural cardiac valve leaflets including inserting a delivery system which includes a sheath covering the prosthesis into a left atrium from the left ventricle, retracting the sheath until the frame of the prosthesis is at least partially uncovered, optionally rotating the delivery system such that commissure anchors are next to corresponding commissures, pulling the delivery system so as to locate a bottom of the frame at the annulus of the heart, and retracting the sheath until rest of the prosthesis is uncovered.

According to some embodiments of the invention, the retracting the sheath until the frame of the prosthesis is at least partially uncovered includes retracting the sheath to expose the commissure anchors.

According to some embodiments of the invention, further including, after retracting the sheath until rest of the prosthesis is uncovered, placing an anchoring extension behind a natural leaflet.

According to an aspect of some embodiments of the present invention there is provided a method of inserting a prosthesis for placing in a cardiac valve to assist operation of natural cardiac valve leaflets including inserting a delivery system which includes a sheath covering the prosthesis into a left atrium from the left ventricle, retracting a portion of the sheath until commissure anchors of the prosthesis are at least partially uncovered, optionally rotating the delivery system such that commissure anchors are next to corresponding commissures, translating the delivery system so as to locate tips of the commissure anchors at the bottom of an annulus of the cardiac valve, and retracting the sheath until rest of the prosthesis is uncovered.

According to some embodiments of the invention, further including, after retracting the sheath until commissure anchors of the prosthesis are uncovered, placing an anchoring extension behind a natural leaflet.

According to an aspect of some embodiments of the present invention there is provided a method of inserting a prosthesis for placing in a cardiac valve to assist operation of natural cardiac valve leaflets including inserting a delivery system which includes a sheath covering the prosthesis into a left ventricle from the left atrium, retracting a portion of the sheath until commissure anchors of the prosthesis are at least partially uncovered, optionally rotating the delivery system such that the commissure anchors are next to corresponding commissures, translating the delivery system so as to locate tips of the commissure anchors at the bottom of an annulus of the cardiac valve, and retracting the sheath until rest of the prosthesis is uncovered.

According to an aspect of some embodiments of the present invention there is provided a device for cardiac valve support including a frame for anchoring the device, configured to be placed upstream of the cardiac annulus and shaped to prevent the frame from shifting downstream of the cardiac valve annulus, and a plurality of anchor extensions attached to the frame, the anchor extensions configured to extend beyond the commissures of the natural cardiac valve and back behind the commissures of the natural cardiac valve, circumventing the commissures without interfering with movement of the natural leaflets, preventing the anchor extensions from shifting back from the downstream side of the annulus to the upstream side of the annulus.

According to some embodiments of the invention, an outer diameter of the frame, at least when expanded, is greater than a diameter of the cardiac annulus.

According to an aspect of some embodiments of the present invention there is provided a device for cardiac valve support including a frame for anchoring the device, configured to be placed upstream of the cardiac annulus and shaped to prevent the frame from shifting downstream of the cardiac valve annulus, and at least one leaflet anchor extension attached to the frame, the leaflet anchor extension configured to extend beyond at least one leaflet of the cardiac valve and back behind the leaflet of the cardiac valve, circumventing the leaflet without interfering with movement of the leaflet, preventing the anchor extension from shifting back from the downstream side of the annulus to the upstream side of the annulus.

According to some embodiments of the invention, the cardiac valve is a mitral valve and the leaflet anchor extension is attached to the frame and is shaped to extend behind a leaflet of the mitral valve which is distant from the aortic valve.

According to some embodiments of the invention, the frame, at least when expanded, has a diameter greater than a diameter of the cardiac annulus.

According to an aspect of some embodiments of the present invention there is provided a device for delivery and deployment of a cardiac valve support including a tip shaped to navigate through a lumen, an inner sleeve shaped to contain at least a portion of the cardiac valve support, and an outer catheter shaped to contain the entire cardiac valve support, wherein the inner sleeve includes a slit through which an anchoring extension of the cardiac valve support may expand when the outer catheter is not surrounding the anchoring extension.

According to some embodiments of the invention, the slit is located in the inner sleeve so as to allow an anchoring extension to expand when the outer catheter is not surrounding the anchoring extension.

According to some embodiments of the invention, the slit includes two slits.

According to some embodiments of the invention, the two slits are located in the inner sleeve so as to allow two commissure anchoring extensions to expand when the outer catheter is not surrounding the anchoring extension.

According to an aspect of some embodiments of the present invention there is provided a device for delivery and deployment of a cardiac valve support including a tip shaped to navigate through a lumen, including a sleeve attached to the tip shaped to contain at least a portion of the cardiac valve support, and a catheter shaped to surround the sleeve and contain the entire cardiac valve support.

According to some embodiments of the invention, the catheter surrounds the sleeve leaving a space at least for an anchoring extension of the cardiac valve.

According to some embodiments of the invention, the catheter surrounds the sleeve leaving a space at least for two commissure anchoring extensions of the cardiac valve.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings.

DESCRIPTION OF SPECIFIC EMBODIMENTS OF THE INVENTION

Figure 1A:
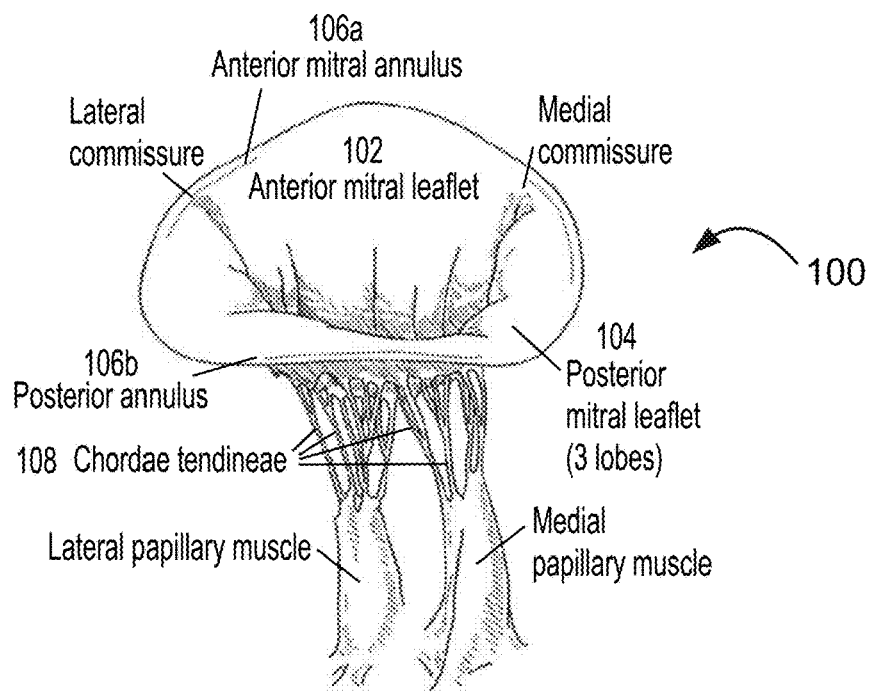
FIG. 1A is a simplified drawing of an example cardiac valve—the mitral valve.

The present invention, in some embodiments thereof, relates to a cardiac valve support, more particularly, but not exclusively, to an assistive prosthesis for a heart valve and, more particularly, but not exclusively, to an assistive prosthesis for a mitral valve.

Introduction

Valves which could theoretically be provided through a non-invasive method, such as the valve taught by U.S. Pat. No. 7,381,220, have many drawbacks. For example, the valves taught are useful for replacement of the functionality of existing valves; however, their installation through non-invasive means is extremely traumatic to the existing native valves. The native valves are known to play an important role in keeping the geometrical structure of the ventricles. When pushed aside by replacement valves that replace their functionality, this task is eliminated, resulting in long term deterioration of the heart chamber, leading to a severe heart failure. Furthermore, the replacement valves themselves, even when installed in a manner that supports existing valve tissue, by replacing its functionality, must still withstand very high pressures. Such high pressures can lead to many different types of problems, including reflux in which blood returns through the heart in a retrograde manner. Furthermore, unlike in surgery, where the anterior leaflet is resectioned to prevent Left Ventricle Outflow Track (LVOT) obstruction, a replacement valve placed via a minimally invasive technique, pushes the anterior leaflet toward the neighboring aortic valve, possibly causing obstruction to the LVOT.

The present invention, in at least some embodiments, relates to a cardiac valve support, such as a support for an artificial mitral valve and/or tricuspid valve prosthesis, which may optionally be inserted through any one or more of a minimally invasive surgical procedure, a "traditional" operative procedure (which may for example involve open heart surgery), and a trans-catheter procedure.

In some embodiments, the cardiac valve support sits on top of a natural valve, anchors itself, at least partly, by extending one or more anchors through the natural valve, but the anchors are designed not to interfere with the natural movement of a leaflet of the natural valve next to which the anchors are placed.

A natural movement of leaflets of the natural valve define a somewhat cylindrical volume in the heart.

In some embodiments, the one or more anchors extend through the natural heart valve commissure and behind the extent of the natural movement of a leaflet.

In some embodiments, the one or more anchors extend through the natural heart valve commissure, beyond the natural leaflet, and behind the extent of the natural movement of a leaflet.

When a cardiac valve support which does interfere with the natural valve is implanted in a patient, the patient potentially immediately start suffering from a deterioration in valve functionality, allowing very little time for implanting a replacement valve on the cardiac vale support.

In some embodiments of the above, the cardiac valve support may be covered with such a material as to prevent blood from entering the atrium from the ventricle.

The present invention, in at least some embodiments, relates to a valve prosthesis, such as a mitral valve and/or tricuspid valve prosthesis, which may optionally be inserted through any one or more of a minimally invasive surgical procedure, a "traditional" operative procedure (which may for example involve open heart surgery), and a trans-catheter procedure.

In some embodiments, the assistive prosthesis is placed over a subject's natural heart valve, allowing movement of the natural heart valve leaflets. The subject's natural heart valve may be defective, allowing some blood to leak back through the natural heart valve during a heart beat cycle. However, the natural leaflets still block much of the blood from retrograding through the natural heart valve. By placing the assistive prosthesis with artificial leaflets, or a flexible sheet, next to the leaflets of the natural heart valve, the assistive prosthesis blocks retrograde blood.

In some embodiments, the assistive prosthesis is kept in place, over the subject's natural heart valve, without interfering with the chordae.

The valve prosthesis, in at least some embodiments, is an optionally non-stented bioprosthesis, optionally attached by means of suture or other means of bonding, to an optionally expandable, frame (platform). In some embodiments, the frame is optionally made from a suitable material, including, without limitation, a metal and/or an alloy, or any type of suitable composite material. The frame can optionally be made of a self expanding material such as Nitinol (nickel/titanium alloy) or some other metal, such as a cobalt/chrome alloy, optionally expanded by a balloon, and/or a radial expander.

The frame optionally engages tissue at, or near, or above a top margin of the native valve (annulus). The native cardiac valve is not removed. The valve prosthesis preferably does not replace the native valve but rather supports its function.

The terms "native valve" and "native valve annulus" are meant to mean herein the valve or valve annulus already present in a subject, as opposed to an artificial valve or artificial valve annulus.

Overview

By placing the assistive prosthesis over leaflets of the natural heart valve, the natural leaflets absorb much of the back pressure, and the assistive prosthesis can be implemented so as to withstand lower forces.

In some embodiments, the assistive prosthesis is anchored in place using smaller, weaker, anchoring compared to contemporary heart valve implants, as the anchors will not be required to bear the full brunt of the backpressure.

In some embodiments, the assistive prosthesis is placed in a subject's heart valve without suturing the prosthesis to the heart.

In some embodiments, the assistive prosthesis is placed in a subject's heart valve and the prosthesis is sutured to the heart.

In some embodiments, the assistive prosthesis is sutured to the heart using less individual stitches than a typical replacement valve, rather than assistive prosthesis, would require, since forces acting on the assistive prosthesis are smaller, as described in more detail below, especially with reference to FIGS. 9 and 10.

In some embodiments, a frame is provided which is designed to provide anchoring for a prosthesis. Example embodiments of such a prosthesis are depicted in FIGS. 5A-5B, 6, 7A-7B, 8A, 8D, 8G and 8H.

In some embodiments, the assistive prosthesis includes a frame which provides anchoring and in some embodiments also shapes a sheet or tube of flexible material, which acts as a valve. Example embodiments of such a prosthesis are depicted in FIGS. 2A-2C, 3A-3C, 3G, 4A-4B, 5A-5B, 6, 7A-7B, 8A-8F, 8J and 11A.

In some embodiments the deployed prosthesis is prevented from shifting downstream, relative to the direction of blood flow, by having the frame include a first anchor section of a wider diameter than the heart valve annulus.

In some embodiments the deployed prosthesis is prevented from shifting back upstream, relative to the direction of blood flow, by having the frame include a second anchor section include extensions configured to extend behind the natural leaflets. In some embodiments the extensions are configured to extend behind the natural leaflets and back toward the cardiac valve annulus. Example embodiments of such extensions are depicted in FIGS. 3G-P, 5A-B, 6, 8A-B, 8D and 8G-J.

In some embodiments one or more of the extensions are configured as weaker anchors, compared to contemporary heart valve implant anchors, as the anchors will not be required to bear the full force of the backpressure.

In some embodiments the anchors are less firmly attached to the heart compared to anchors of contemporary heart valve implants, as the anchors will not be required to bear the full force of the backpressure.

In some embodiments the anchors are not sutured to the heart as the anchors will not be required to bear the full force of the backpressure.

In some embodiments, the anchoring extensions are configured so that when the prosthesis is in place, the extensions are located next to the cardiac valve commissures, and do not interfere, or interfere just a little, with natural closing and opening of the natural leaflets. Example embodiments of such extensions are depicted in FIGS. 3A-C, 3G-P, 5A-B, 6, 8A-B, 8D and 8G-8J. It is noted that if the extensions interfere just a little with natural movement of the natural leaflets, the prosthesis can still lower backflow through the valve, such as mitral regurgitation, compared to the same heart before receiving the prosthesis valve.

In some embodiments, one or more anchoring extensions are configured to extend downstream beyond the natural leaflet, and go back up behind the natural leaflet. In some embodiments, the curve is configured to allow the natural leaflet a range of motion, so that the natural leaflet will indeed at least partially close the natural valve, picking up some of the backpressure, allowing the prosthesis to perform a complete closure of the valve and to pick up just some of the backpressure. Example embodiments of such extensions are depicted in FIGS. 3G-P, 5A-B, 6, 8A, 8D and 8G-I.

In some embodiments, extensions, termed herein posts, are attached to the frame and extend within the sheet of flexible material which acts as the assistive valve. The extensions extend beyond the annulus of the cardiac valve, and prevent the sheet from collapsing back from the downstream side of the annulus to the upstream side of the annulus. The extensions acting to prevent the sheet from collapsing back are termed herein posts, so as to differentiate them from anchoring extensions.

In some embodiments, the posts are configured so that when the prosthesis is in place, the posts are located at the cardiac valve commissures. Such posts interfere little with natural closing and opening of the natural leaflets. Example embodiments of such extensions are depicted in FIGS. 3A, 3C, 3G-3P, 4A-B, 5A-B, 6, 7A-B, 8A-B, 8D, 8G-H, 8J and 11A.

In some embodiments, the posts are on the inside of the flexible sheets, preventing an annulus formed from the flexible sheets from collapsing upstream.

In some embodiments, the posts are on the outside of the flexible sheets, and attached to the flexible sheets, preventing an annulus formed from the flexible sheets from collapsing upstream.

In some embodiments, the anchoring extensions are on the outside of the flexible sheets, enabling the anchoring extensions to contact the heart and provide anchoring.

For purposes of better understanding some embodiments of the present invention, as illustrated in FIGS. 2A-2C, 3A-3R, 4A-4B, 5A-5B, 6, 7A-7B, 8A-8J and 11A of the drawings, reference is first made to FIG. 1A, which is a simplified drawing of an example cardiac valve—the mitral valve 100.

FIG. 1A depicts the mitral valve 100, which has two valve leaflets 102 104. Base edges of the valve leaflets are attached to the heart along the mitral valve annulus 106a 106b. Tips of the valve leaflets are attached to the ventricle walls by chords 108.

Figure 1B:
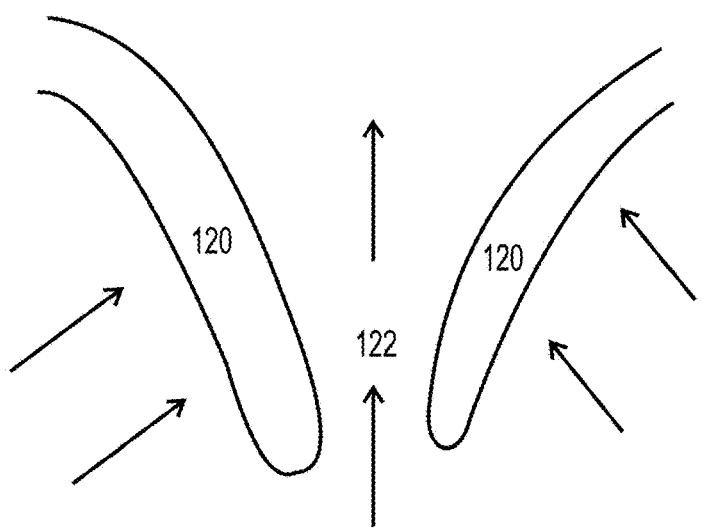
FIG. 1B is a simplified cross-sectional drawing of leaflets of a cardiac valve, which show what happens when the leaflets fail to coapt and fail to block reverse flow of blood.

Reference is now made to FIG. 1B, which is a simplified cross-sectional drawing of leaflets 120 of a cardiac valve, which show what happens when the leaflets 120 fail to coapt and fail to block reverse flow 122 of blood.

Before explaining at least one embodiment of the invention in detail, it is to be understood that the invention is not necessarily limited in its application to the details of construction and the arrangement of the components and/or methods set forth in the following description and/or illustrated in the drawings and/or the images. The invention is capable of other embodiments or of being practiced or carried out in various ways.

Figure 2A:
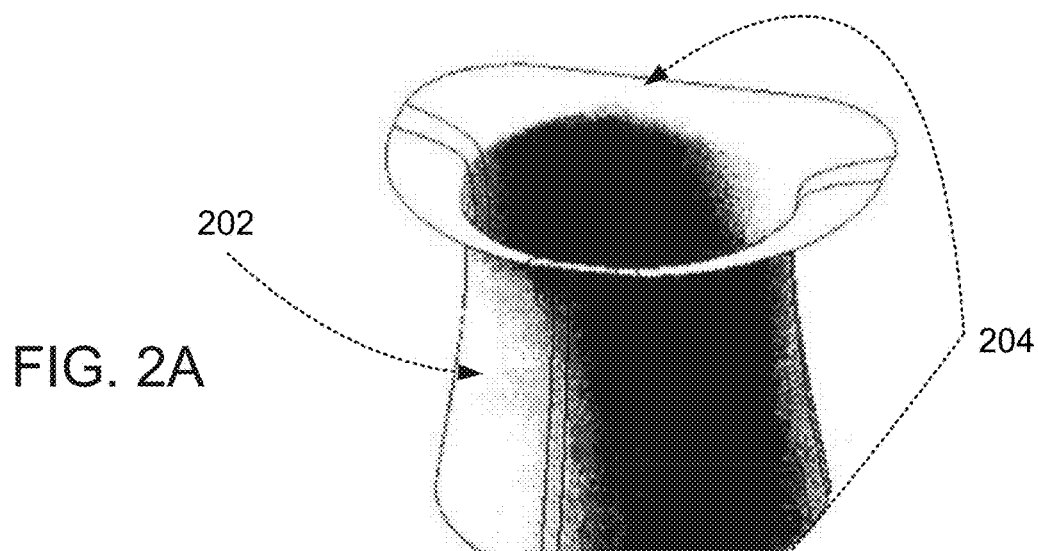
FIG. 2A is a simplified drawing of a sheet of flexible material for attaching to a frame according to an example embodiment of the invention.

Reference is now made to FIG. 2A, which is a simplified drawing of a sheet 202 of flexible material for attaching to a frame (not shown) according to an example embodiment of the invention. The sheet 202 is configured to be placed within the annulus of the cardiac valve (not shown), defining a lumen 204 of the sheet extending from an upstream side of the annulus to a downstream side of the annulus.

In some embodiments the sheet 202 is made of a single piece of a flexible material, shaped as a generally tube-like section.

In some embodiments the sheet 202 is made of several pieces of a flexible material connected together.

In some embodiments the sheet 202 is made of several pieces of a flexible material configured to be similar to cardiac leaflets surrounding a central lumen.

In some embodiments, the valve prosthesis optionally features a flexible film made of biological tissue such as pericardia tissue but may also optionally feature one or a combination of synthetic materials, additionally or alternatively.

The flexible material is preferably flexible enough to be moved by movement of the natural leaflets, preferably without interfering with movement of the natural leaflets.

In some embodiments the flexible sheet preferably has a shape that is generally made of 2 leaflets. The flexible sheet may optionally have a variable diameter which enables flow in one direction, for example from the atrium to the ventricle. In the example, when the ventricle contracts, the valve closes and blocks return flow from the ventricle to the atrium. If such retrograde flow is allowed, the retrograde flow potentially poses danger; over a prolonged period of time, the retrograde flow can lead to many deleterious health effects, including a deleterious effect on the overall health of the heart muscle.

In some embodiments, the valve prosthesis features a "skirt" which preferably does not, or minimally, restricts motion of the native valve leaflets, and which is optionally situated on top of the leaflets, for example in the direction of the atrium. "On top" is meant with regard to a direction of normal, not retrograde, blood flow. Even if the natural leaflets were to prolapse into the atrium, blood would be prevented from flowing into the atrium since the skirt is on top of the native valve leaflets, and the skirt closes a gap between the natural leaflets, blocking retrograde blood flow.

In an embodiment, the "skirt" is optionally in a shape of the native valve (e.g. generally a D shape) with a diameter that may vary and which is optionally and more preferably used to complete the incompetent closure of the native valve as a whole. Thus, the skirt specifically and the valve prosthesis generally are preferably not intended to be used as a replacement to the entire valve or in addition to only one native leaflet (in contrast to the apparatus described by Macoviak et al in US application 2008/0065204, for example). In some embodiments, the valve skirt is preferably reinforced with at least one reinforcement along at least a portion of its length, in order to prevent prolapse of the skirt into the left atrium. This reinforcement is optionally preferably an extension from the frame (not shown).

Figure 2B:
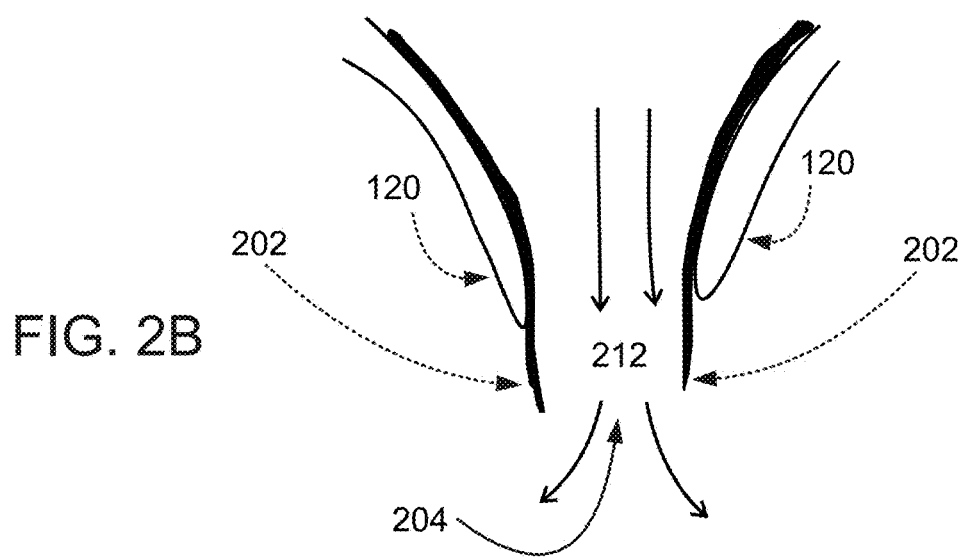
FIG. 2B is a simplified cross sectional drawing of the leaflets of FIG. 1B and the sheet of FIG. 2A, in an example embodiment of the invention, when pressure is upstream of the cardiac valve.

Reference is now made to FIG. 2B, which is a simplified cross sectional drawing of the leaflets 120 of FIG. 1B and the sheet 202 of FIG. 2A, in an example embodiment of the invention, when pressure is upstream of the cardiac valve.

FIG. 2B depicts what happens when pressure is upstream of the cardiac valve: the leaflets 120 are pushed open, and the sheet 202 is pushed open, and blood flows 212 through the lumen 204 of the sheet 202.

Figure 2C:
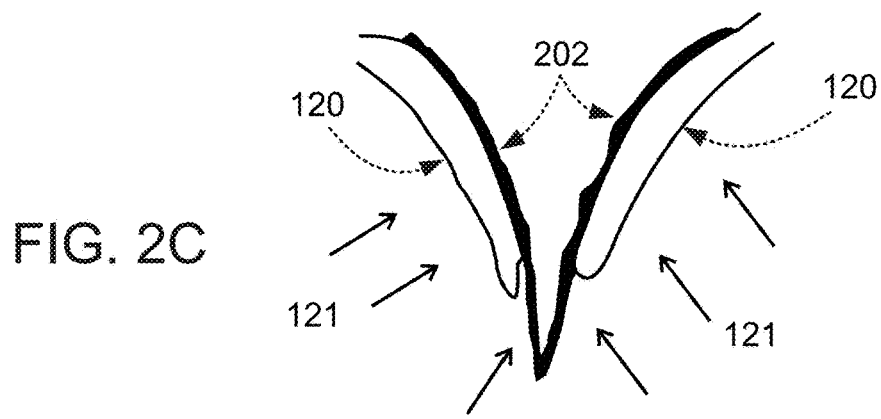
FIG. 2C is a simplified cross sectional drawing of the leaflets of FIG. 1B and the sheet of FIG. 2A, in an example embodiment of the invention when pressure is downstream of the cardiac valve.

Reference is now made to FIG. 2C, which is a simplified cross sectional drawing of the leaflets 120 of FIG. 1B and the sheet 202 of FIG. 2A, in an example embodiment of the invention when pressure is downstream of the cardiac valve.

FIG. 2C depicts what happens when pressure is downstream of the cardiac valve. The leaflets 120 are pushed toward closing.

In some cases, such as depicted in FIG. 2C, the leaflets 120 do not fully coapt, that is, do not fully close. The sheet 202 is pushed closed, and blood does not flow through the lumen 204 of the sheet 202.

The leaflets 120 are pushed against the sheet 202, so that blood does not leak back between the sheet 202 and the leaflets 120.

During systole, the action of the native valve leaflets is to close the passage between, for example, the left ventricle and the left atrium. In some embodiments, the natural leaflets 120, while acting as such, press against the sheet 202, producing a natural barrier preventing blood from passing from the left ventricle to the left atrium around the circumference of the prosthesis, thus effectively sealing and preventing para-valvular leaks.

The leaflets 120 are pushed against the sheet 202, so the leaflets 202 pick up some of the backpressure 121.

Some Example Embodiments in More Detail

Figure 3A:
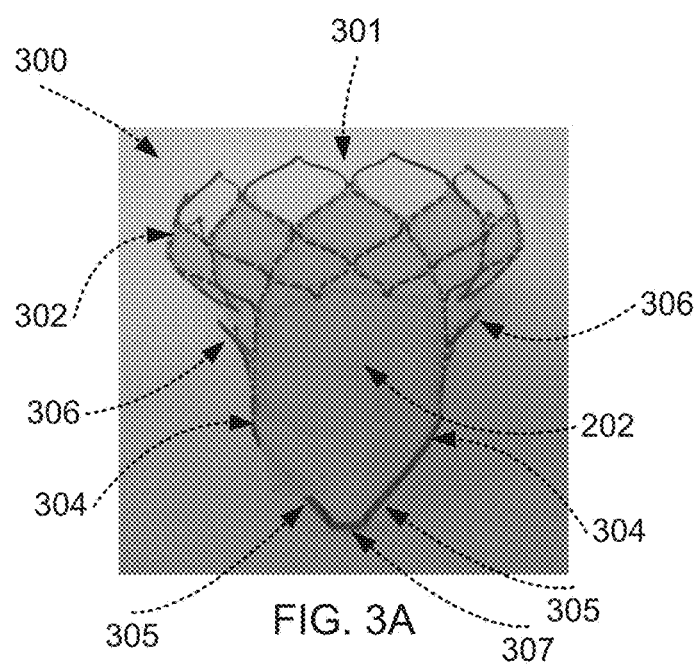
FIG. 3A is a side view image of a cardiac valve prosthesis according to an example embodiment of the invention.

Reference is now made to FIG. 3A, which is a side view image of a cardiac valve prosthesis according to an example embodiment of the invention.

FIG. 3A depicts a device 300 including a frame 302 and the flexible sheet 202, and a direction of normal flow 301 through the device. The flexible sheet 202 of the example embodiment of FIG. 3A is attached to the frame 302 at many points. In some embodiments the flexible sheet 202 is sewn to the frame 302.

Also depicted are two posts 304, attached to the frame 302 and to the flexible sheet 202. In the example embodiment depicted in FIG. 3A, the two posts are attached to each other at their downstream end 305.

In some embodiments, the distance between bases of the posts 304, where they are attached to the frame 302, is greater than the distance between the downstream ends of the posts 305. In some embodiments the downstream ends of the posts 305 are not connected to each other (not shown). In some embodiments the downstream ends of the posts 305 are connected, as depicted in FIG. 3A. In some embodiments the two posts 305 are connected by a connecting extension 307 at an angle to the downstream ends of the posts 305. In some embodiments, the connecting extension 307 is at an angle to the downstream ends of the posts 305, but not perpendicular to the downstream ends of the posts 305 due to material bending considerations.

Having two posts in a mitral valve prosthesis corresponds to the mitral valve having two commissures at the meeting edges of two natural leaflets.

In some embodiments, a prosthesis for heart valve which has three natural leaflets may have two posts, optionally positioned at meetings of two of the three natural leaflets.

In some embodiments, a prosthesis for heart valve which has three natural leaflets may have three posts, optionally positioned at meetings of the three natural leaflets. The skirt, for example the sheet 202 of flexible material of FIG. 3A, is then shaped to completely close under pressure from the three natural leaflets.

In some embodiments, the flexible sheet 202 is connected to the posts 304, and the posts help prevent the flexible sheet 202 from inverting back upstream under back pressure. In medical terms, a leaflet inverting back upstream is called prolapse. In the sample embodiment depicted in FIG. 3A, the flexible sheet 202 is connected to the posts 304 only along part of the length of the posts, enough to prevent inverting, and also enough to retain freedom of movement for a downstream end of the flexible sheet 202.

In some embodiments, the freedom of movement is enough to allow 2 mm, 3 mm, 4 mm, 5 mm, or even more coaptation height along the skirt, or flexible sheet 202.

Also depicted are two anchor extensions 306, attached to the frame 302.

In the example embodiment depicted in FIG. 3A, the two anchor extensions 306 are located at positions which are suitable for extending behind the commissures of the cardiac valve, making the two anchor extensions 306 of FIG. 3A examples of what is termed commissure anchor extensions.

In the example embodiment depicted in FIG. 3A, the two anchor extensions 306 are attached to the frame 302 by virtue of being attached to the posts 304, which are connected to the frame 302. Attaching anchor extension to posts rather than directly to the frame, or attaching posts to anchor extension rather than directly to the frame, are both possible options. The options are especially relevant when the posts are at natural commissures, and the anchor extensions are designed to be at the commissures.

In some embodiments the frame 302 depicted in FIG. 3A is self expanding, so as to conform to the shape of the surrounding tissue and so as to move with the surrounding tissue.

The frame 302, and the prosthesis device is preferable strong enough to withstand hundreds of millions of flex cycles, corresponding to hundreds of millions of heartbeats. For example, the prosthesis device is preferable stiff enough to withstand 400 M-800 M cycles, corresponding to 10-15 years or more of heartbeats.

Figure 3B:
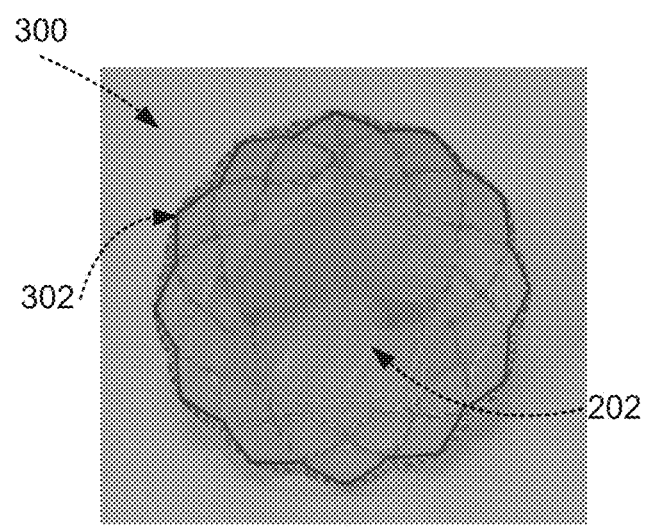
FIG. 3B is a top view image of the cardiac valve prosthesis also depicted in FIG. 3A.

Reference is now made to FIG. 3B, which is a top view image of the cardiac valve prosthesis also depicted in FIG. 3A.

FIG. 3B depicts the device 300, the frame 302, and the flexible sheet 202. The direction of normal flow through the device is from the observer into the page.

In the example embodiment depicted in FIGS. 3A and 3B the flexible sheet 202 is attached to the frame 302 at the inside of the frame 302.

Figure 3C:
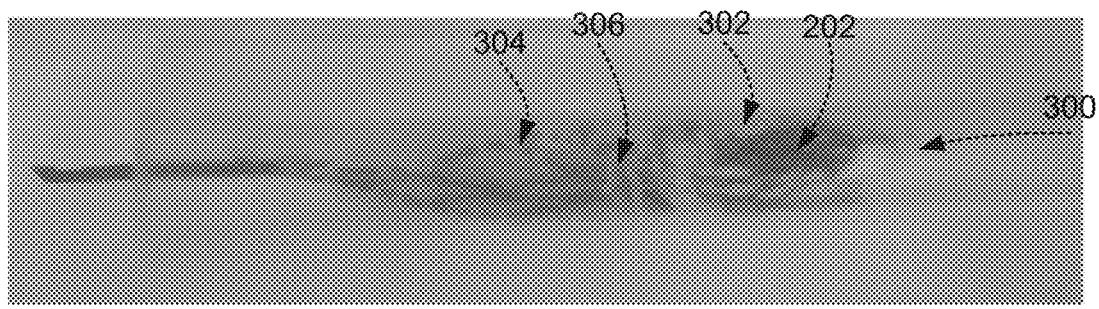
FIG. 3C is a side view image of the cardiac valve prosthesis also depicted in FIG. 3A.

Reference is now made to FIG. 3C, which is a side view image of the cardiac valve prosthesis also depicted in FIG. 3A.

FIG. 3C depicts the device 300; the frame 302; the flexible sheet 202; the posts 304; and the anchor extensions 306, as they appear when compressed for delivery into a heart via a catheter.

According to some embodiments, the device 300 comprises a support structure featuring a deployable construction adapted to be initially collapsed (crimped) in a narrow configuration suitable for introduction through a small puncture or incision into the heart cavity such as the left ventricle, the left atrium, the right atrium, the right ventricle and so forth, thereby providing access to the target location. The device 300 is optionally further adapted to be deployed by means of removing a radial constriction such as a sheath to allow the device 300 to self-expand to its deployed state in the target location.

According to some embodiments, at least some of the frame of the device expands and/or is expanded to a diameter greater than a diameter of the cardiac annulus. The expansion of the frame potentially prevents the frame from slipping beyond the cardiac annulus after the expansion.

Figure 3D:
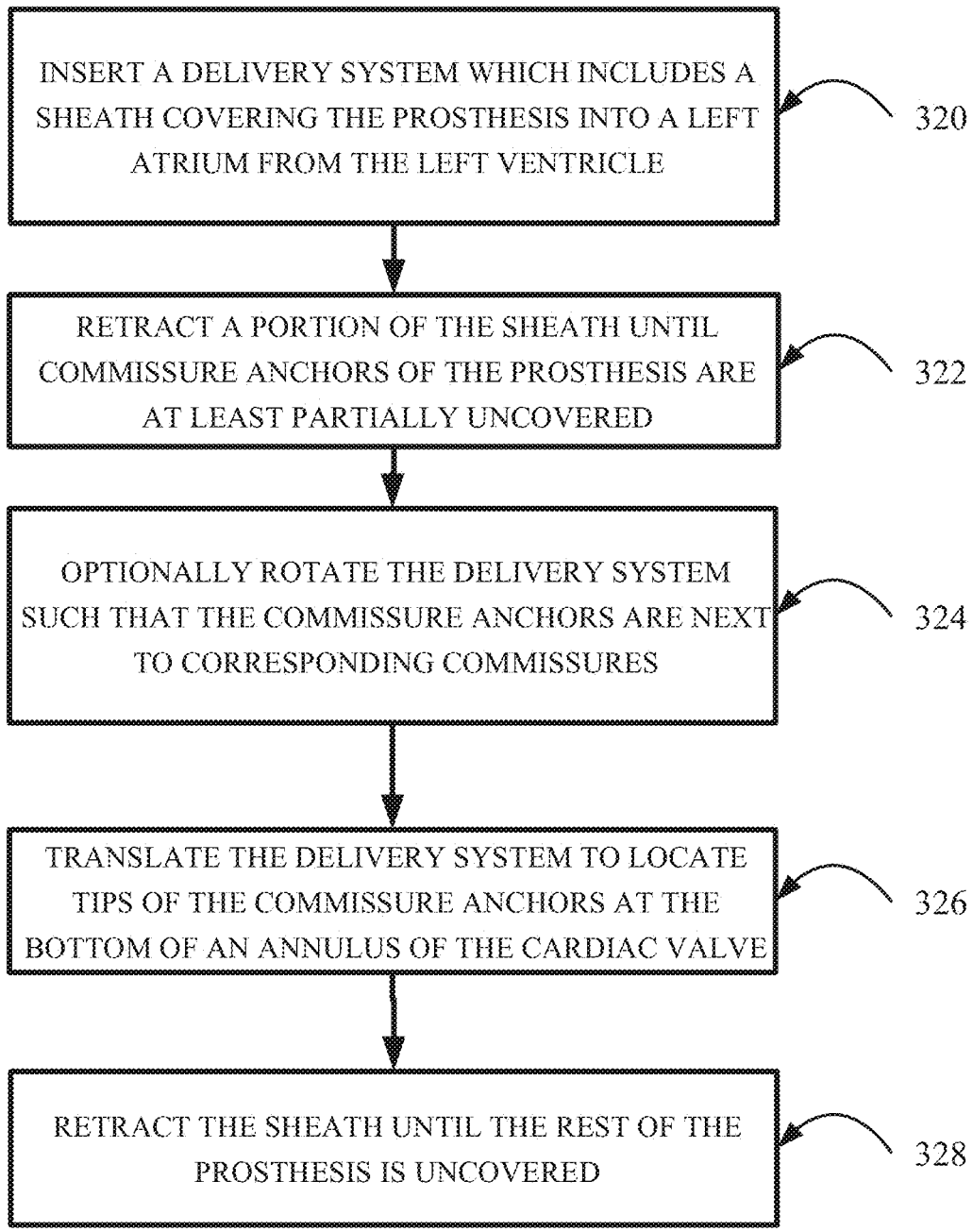
FIG. 3D is a simplified flow chart illustration of a method of inserting a prosthesis for placing in a cardiac valve to assist operation of natural cardiac valve leaflets, according to an example embodiment of the invention.

Reference is now made to FIG. 3D, which is a simplified flow chart illustration of a method of placement of an example embodiment of a prosthesis in a heart according to an example embodiment of the invention.

The method illustrated by FIG. 3D includes:

inserting a delivery system which includes a sheath covering the prosthesis into a left atrium from the left ventricle (320); retracting the sheath until commissure anchors of the prosthesis are at least partially uncovered (322);

optionally rotating the delivery system such that the commissure anchors are next to corresponding commissures (324);

translating (optionally pushing or pulling) the delivery system so as to locate tips of the commissure anchors at the bottom of an annulus of the cardiac valve (326); and retracting the sheath until rest of the prosthesis is uncovered (328).

Additional optional actions may be taken during and after performing the above procedure.

Ultrasound imaging and/or other methods of visualization may optionally be taken in order to perform the optional rotation to visualize commissure anchors and/or the natural commissures.

After pulling the delivery system so as to locate a bottom of the frame at the annulus of the heart as described in reference number 326, the delivery system may be optionally be additionally pulled to assist anchoring extensions to deploy sideways on the ventricular side of the annulus.

Figure 5A:
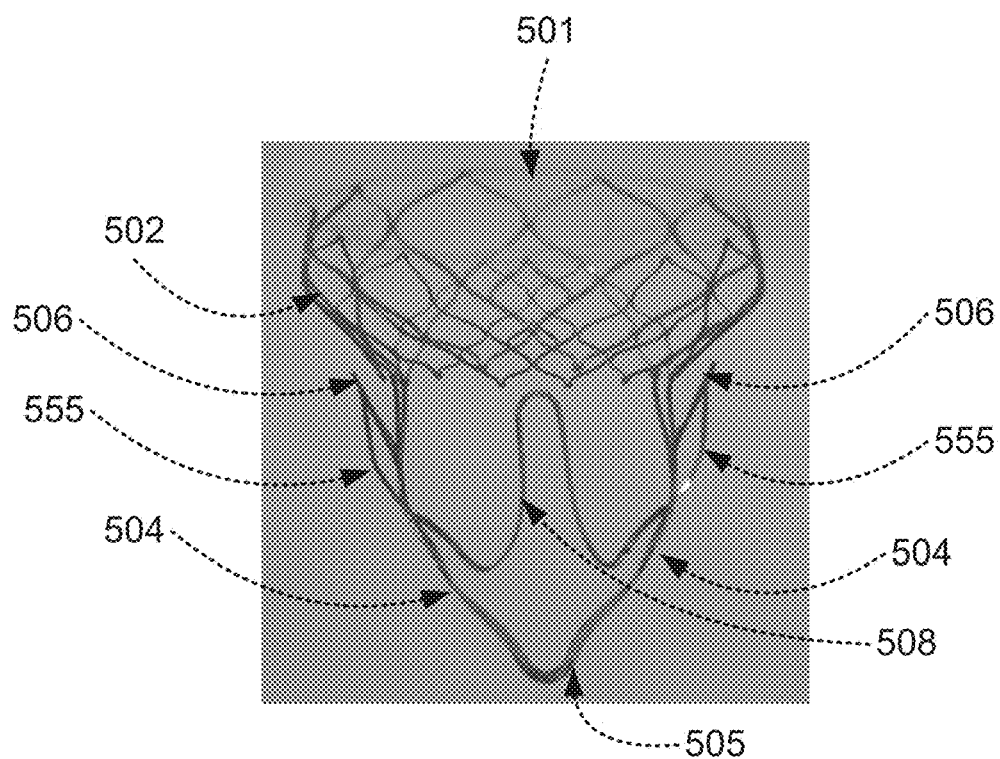
FIG. 5A is a side view image of a cardiac valve support according to an example embodiment of the invention.

Optionally, additional actions may be taken to assist anchor extensions, such as optionally positioning the anchor extension 508 of FIG. 5A to be behind a native leaflet, such as the posterior leaflet, preferably free of chordea entanglements.

Optionally, flow and pressure measurements may be performed across the prosthesis.

Optionally final disengagement of the delivery system from the prosthesis may still be performed.

The above described method of placement of an example embodiment of a prosthesis in a heart are not meant to be limiting, rather the method is intended to serve as an example on which variations can be made.

Some example variations on the above described method are now described.

Different embodiments of the invention use different ways of getting the prosthesis into the heart. Some non-limiting example ways include:

trans-apical: through the apex of the heart (heart muscle) directly into the left ventricle (LV) and to the left atrium (LA);

atrial: directly to the LA and into the LV;

transfemoral: transeptal into the LA and to the LV.

The delivery method for the prosthesis may be inserted from the left ventricle into the left atrium. Getting to the left ventricle may be done via a puncture in the apex of the left ventricle, via a puncture in the left ventricle wall, via the left atrium (via the LA/RA septum or LAA), or via the aorta.

If the prosthesis is a self-expanding prosthesis, being made, by way of a non-limiting example, of a springy material, and/or of a memory material, pulling the sheath and uncovering the frame and/or the rest of the prosthesis may be enough to allow the prosthesis to expand to its intended shape. If the prosthesis is not a self-expanding prosthesis, after the pulling of the sheath a process of expanding the frame and/or the rest of the prosthesis, such as posts and/or anchoring extensions, is performed.

In some embodiments, rotating the delivery system such that commissure anchors are next to corresponding commissures may not be needed. For example, in some embodiments, at least part of the frame, corresponding to the natural heart annulus, forms a D-shaped annulus, and the D-shape of the frame annulus can align the prosthesis with the annulus of the heart so that rotation may not be needed.

In some embodiments the prosthesis is located in the annulus of the heart before the first pulling of the sheath is performed, and prosthesis is rotated to align the commissure anchors to the commissures, and the location of the anchors to be below the annulus while the frame is above and/or next to the annulus of the heart, and the pulling of the sheath is performed in one pull, which uncovers both the frame and the rest of the prosthesis in their corresponding locations.

An example embodiment, in which access to the mitral valve is obtained from an opposite direction than was described above with reference to FIG. 3D, is now described.

Figure 3E:
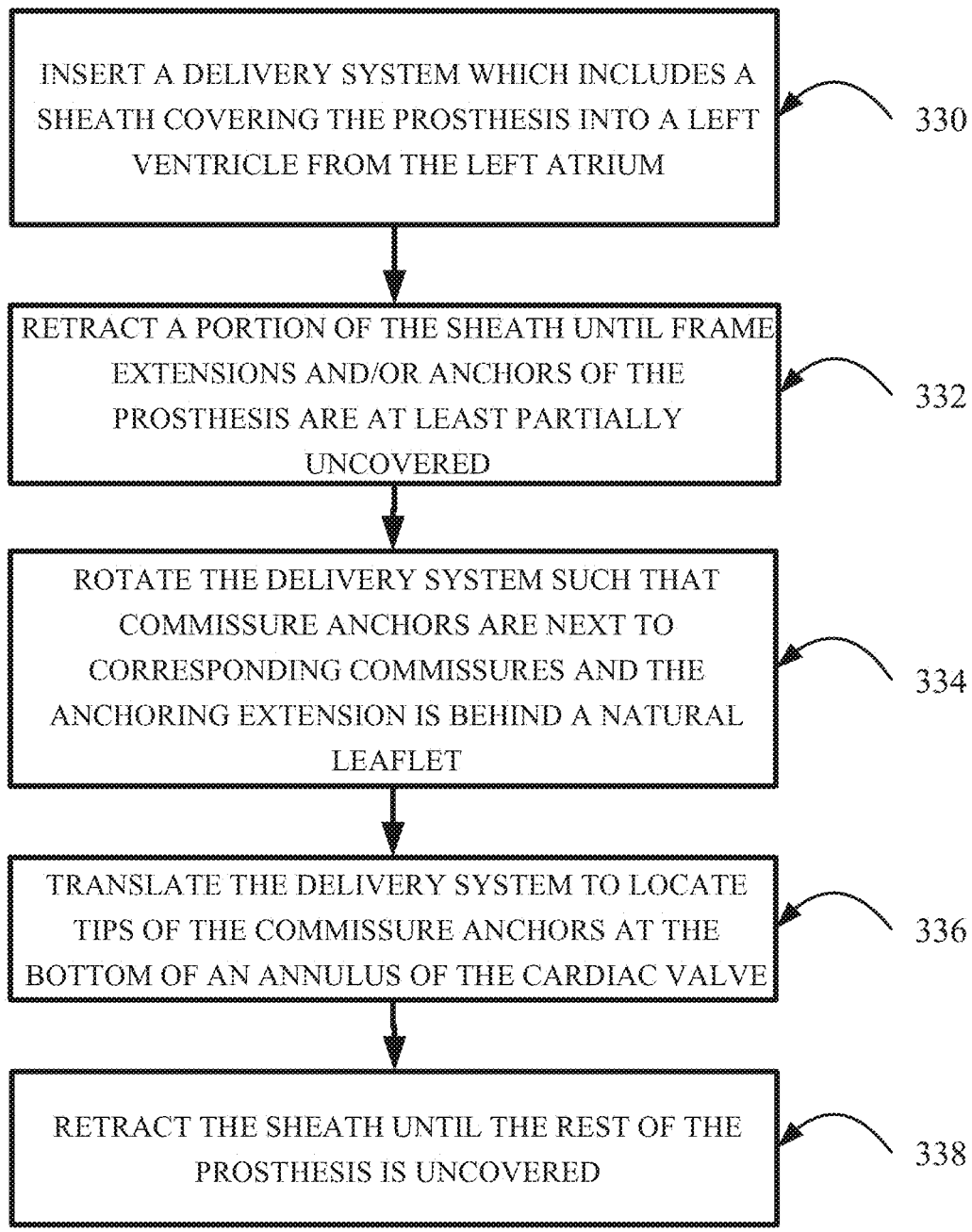
FIG. 3E is a simplified flow chart illustration of another method of inserting a prosthesis for placing in a cardiac valve to assist operation of natural cardiac valve leaflets, according to an example embodiment of the invention.

Reference is now made to FIG. 3E, which is a simplified flow chart illustration of another method of inserting a prosthesis for placing in a cardiac valve to assist operation of natural cardiac valve leaflets, according to an example embodiment of the invention.

Figure 5B:
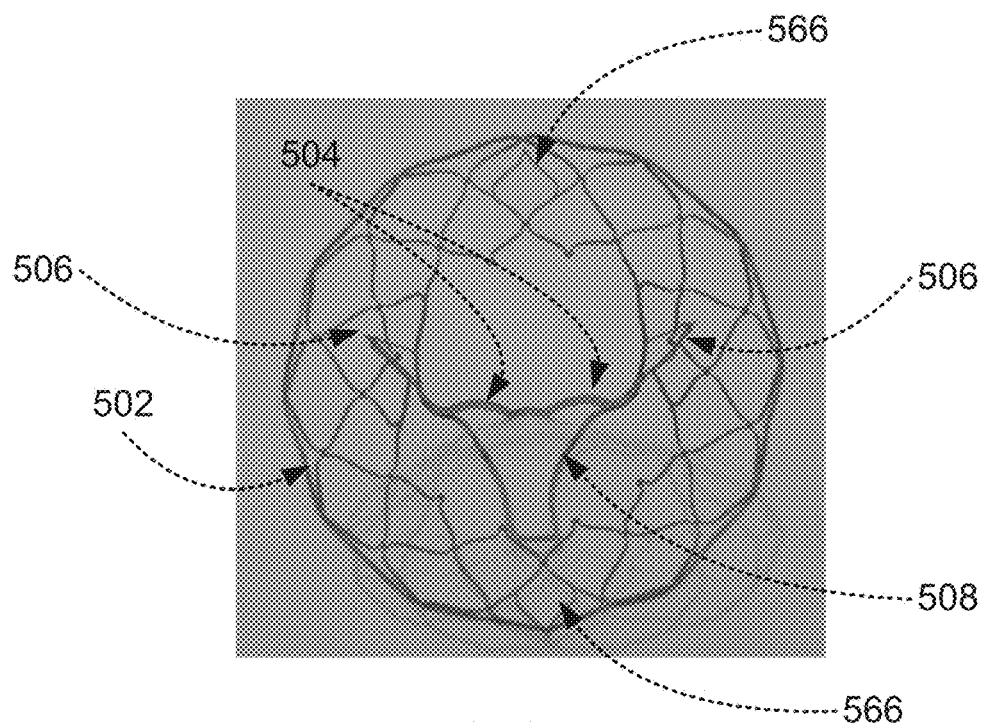
FIG. 5B is a top view image of the cardiac valve support also depicted in FIG. 5A.

The method illustrated by FIG. 3E includes:

inserting a delivery system which includes a sheath covering the prosthesis into a left ventricle from the left atrium (330);

retracting a portion of the sheath until frame extensions and/or anchors of the prosthesis are at least partially uncovered (332);

optionally rotating the delivery system such that commissure anchors are next to corresponding commissures and the anchoring extension 508 of FIGS. 5A-5B is behind a natural cardiac leaflet (334);

translating (optionally pushing or pulling) the delivery system so as to locate tips of the commissure anchors at the bottom of an annulus of the cardiac valve (336); and retracting the sheath until rest of the prosthesis is uncovered (338).

It is noted that the method described by FIG. 3E is suitable for entry into a left ventricle from the atrium, and also for entry into a left ventricle through the apex of the heart (heart muscle) in what is called a trans-apical approach.

Additional optional actions may be taken during and after performing the above procedure, similarly to the actions described above with reference to FIG. 3D.

Figure 3F:
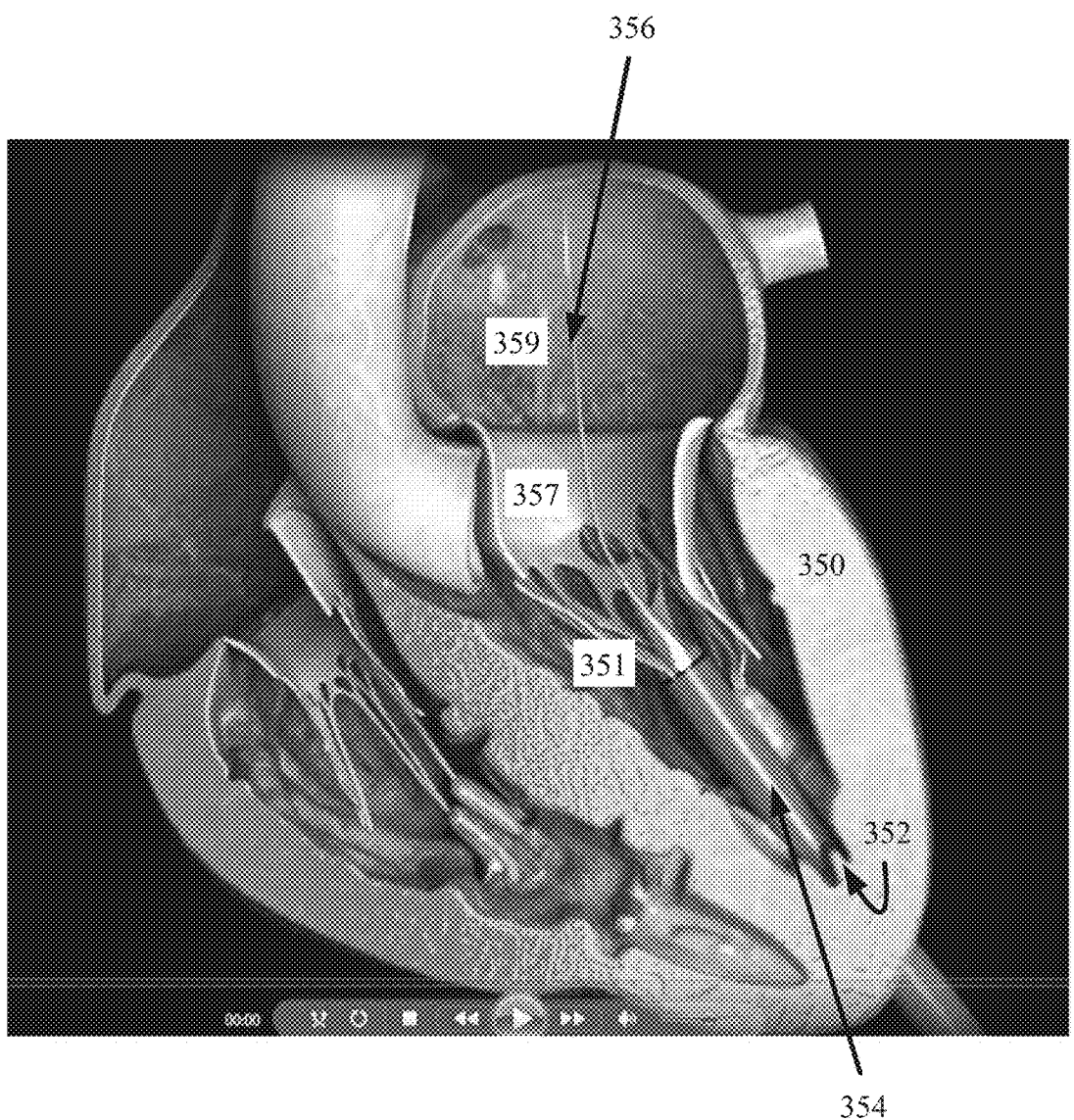
FIG. 3F is a simplified illustration of a method of inserting a cardiac valve prosthesis to assist a mitral valve, via a trans-apical approach, according to an example embodiment of the invention.

Reference is now made to FIG. 3F, which is a simplified illustration of a method of inserting a cardiac valve prosthesis to assist a mitral valve, via a trans-apical approach, according to an example embodiment of the invention.

FIG. 3F depicts a catheter having a sheath 354 and a guide wire 356, inserted into a left ventricle 351 via a puncture 352 in the apex of a heart 350. FIG. 3F depicts the guide wire 356 reaching through the mitral valve 357 into the left atrium 359.

FIG. 3F depicts the prosthesis still within the sheath 354, so not visible in FIG. 3F, and the catheter may even be pushed further into the left atrium during deployment, in order to introduce at least part of the frame of the prosthesis at and/or above the mitral valve 357.

Figure 3G:
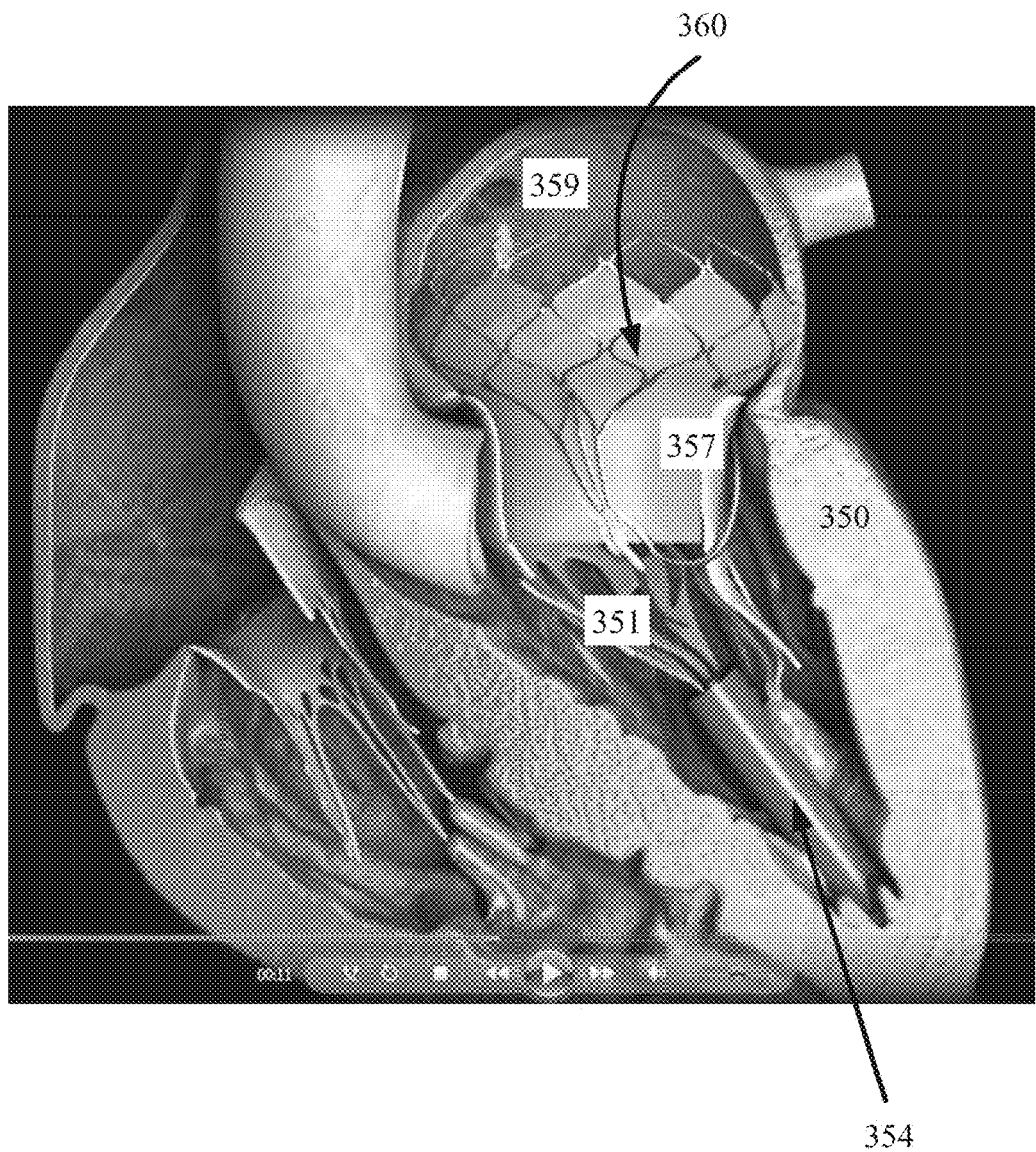
FIG. 3G is a simplified illustration of the method of FIG. 3F, with the sheath retracted and the cardiac valve prosthesis deployed and visible.

Reference is now made to FIG. 3G, which is a simplified illustration of the method of FIG. 3F, with the sheath 354 retracted and the cardiac valve 360 deployed and visible.

FIG. 3G depicts the catheter with the sheath 354 still within the left ventricle 351 of the heart 350, and with the cardiac valve 360 deployed to assist the mitral valve 357.

Reference is now made to FIGS. 3H-3O, which are a simplified illustration of a process of pushing a cardiac valve support out of an insertion catheter according to an example embodiment of the invention.

Figure 3H:
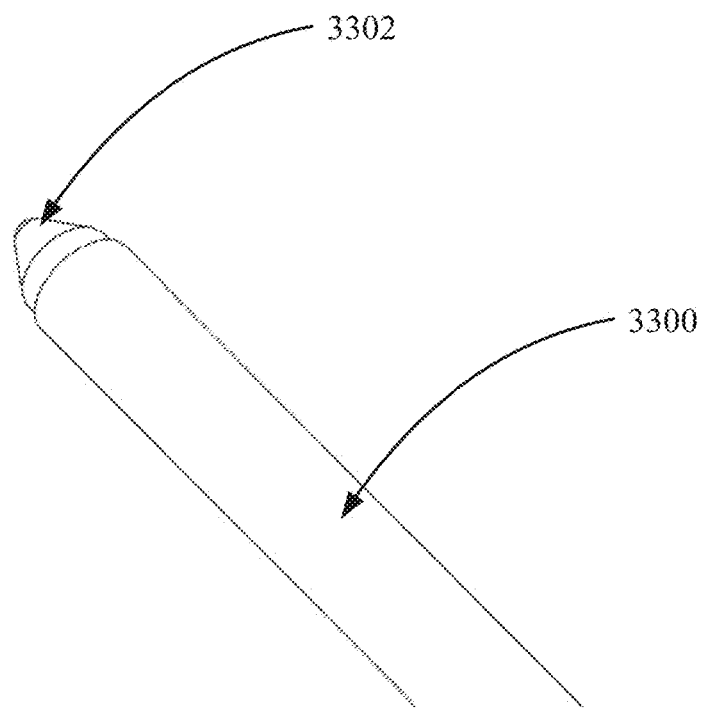
FIGS. 3H-3M are a simplified illustration of a process of pushing a cardiac valve support out of an insertion catheter according to an example embodiment of the invention.

FIG. 3H depicts a catheter 3300 having a tip 3302 shaped to navigate through blood vessels (lumens).

Figure 3I:
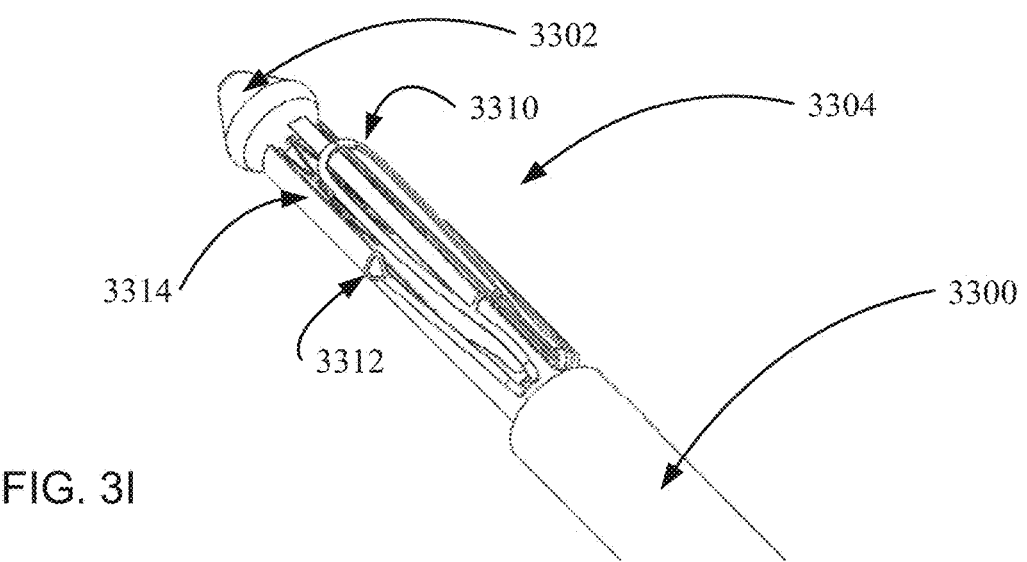

FIG. 3I depicts the catheter 3300 pulled back from the tip 3302 exposing at least part of a cardiac valve support 3304. FIG. 3I also depicts a sleeve 3314, inside of which is a frame component (not referenced in FIG. 3I) of the cardiac valve support 3304, and outside of which are an anchor extension 3310 and a commissure extension 3312.

In some embodiments the sleeve 3314 includes slits, as shown in FIG. 3I, through which the anchor extension 3310 and/or commissure extension 3312 can optionally expand.

Figure 3J:
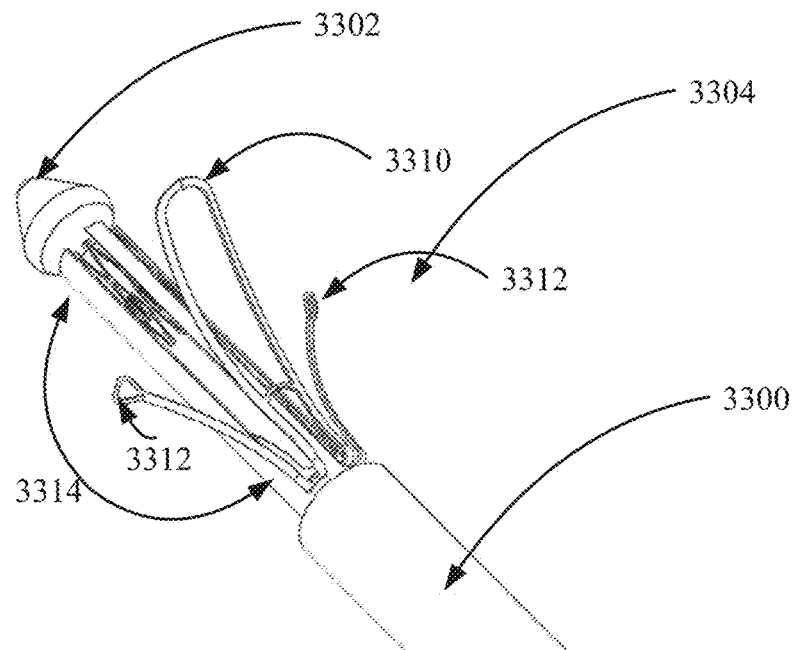

When the tip 3302, the sleeve 3314 and the cardiac valve support 3304 are extended from the catheter 3300, as depicted in FIG. 3I, the anchor extension 3310 and/or the commissure extension 3312 optionally expand, as will be depicted in FIG. 3J, whilst the frame component of the cardiac valve support 3304 remains compressed inside the sleeve 3314.

In some embodiments, the sleeve 3314 includes one slit, and the sleeve 3314 is gradually rotated so as to release the anchor extension 3310 and/or the commissure extension 3312 one at a time, potentially allowing the anchor extension 3310 and/or the commissure extension 3312 to expand one at a time. Having the anchor extension 3310 and/or the commissure extension 3312 expand one at a time potentially allows a surgeon to control placement of the anchor extension 3310 and/or the commissure extension 3312 relative to the heart one at a time.

In some embodiments, the sleeve 3314 includes more than one slit, and the anchor extension 3310 and/or the commissure extension 3312 are released one at a time, potentially allowing the anchor extension 3310 and/or the commissure extension 3312 to expand one at a time.

FIG. 3J depicts the tip 3302 extended from the catheter 3300, and the sleeve 3314 covering some parts of the cardiac valve support 3304, and hiding them from view. FIG. 3J depicts the insertion catheter 3300 after the catheter 3300 had optionally been pulled back from the tip 3302 enough to release the anchor extension 3310 and the commissure extensions 3312.

Figure 3K:
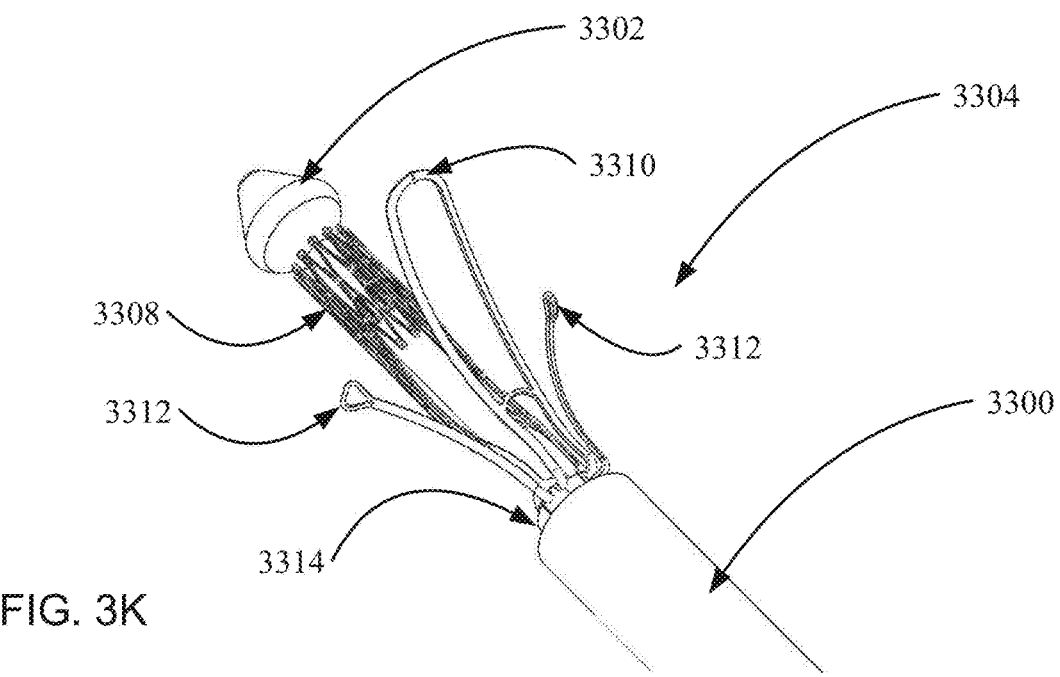

FIG. 3K depicts the components of FIG. 3J, with the sleeve 3314 retracted into the catheter 3300, releasing the frame 3308 of the cardiac valve support 3304. FIG. 3K also depicts the anchor extension 3310 and commissure extensions 3312, and a frame 3308 of the cardiac valve support 3304, similar to the frame 302 of FIG. 3A.

Figure 3L:
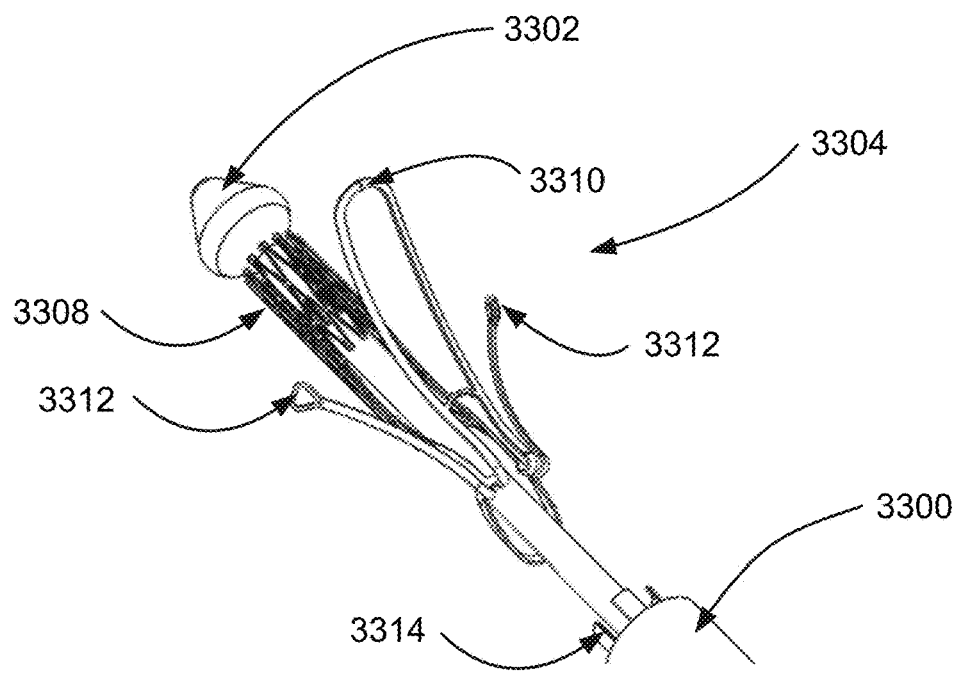

FIG. 3L depicts the catheter 3300 with the sleeve 3314 and the catheter 3300 pulled further back relative to the tip 3302. FIG. 3L also depicts the frame 3308 of the cardiac valve support 3304, the anchor extension 3310 and commissure extensions 3312. The anchor extension 3310 and the commissure extensions 3312 are depicted starting to expand.

Figure 3M:
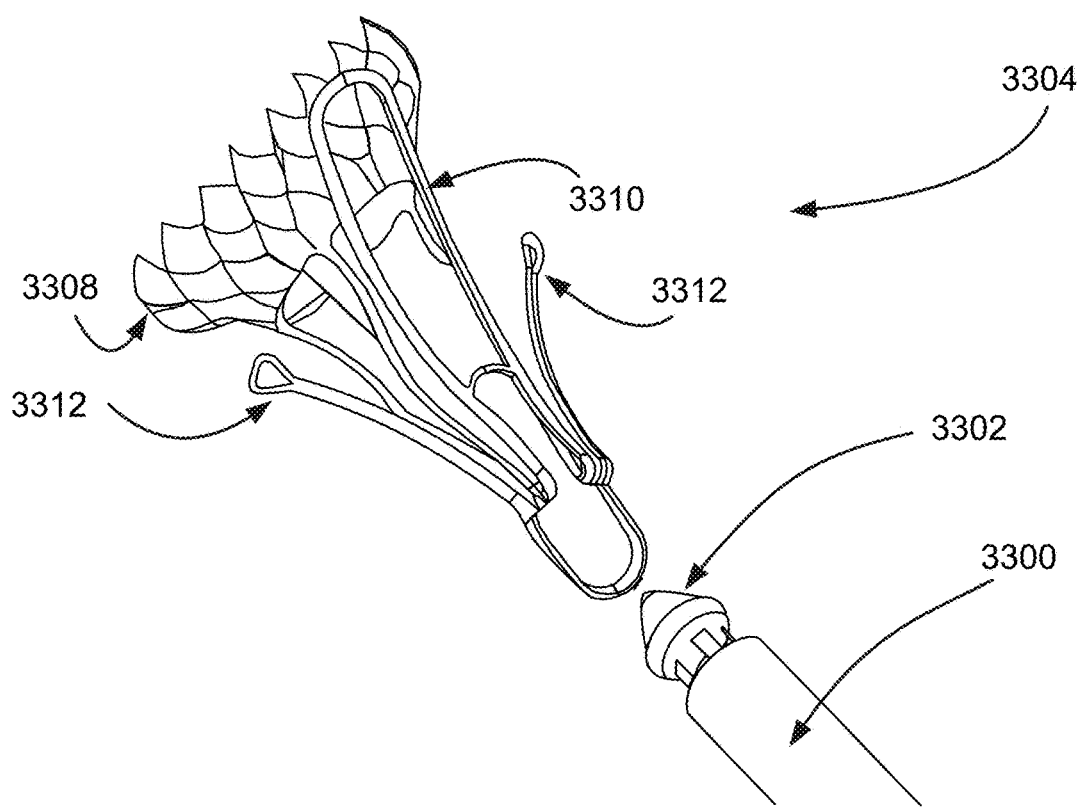

FIG. 3M depicts the catheter 3300 with the tip 3302 pulled back through the center of the cardiac valve support 3304, and the cardiac valve support 3304 released from the catheter 3300. FIG. 3M also depicts the frame 3308 of the cardiac valve support 3304, the anchor extension 3310 and commissure extensions 3312. The frame 3308 is depicted in an expanded state.

Figure 3N:
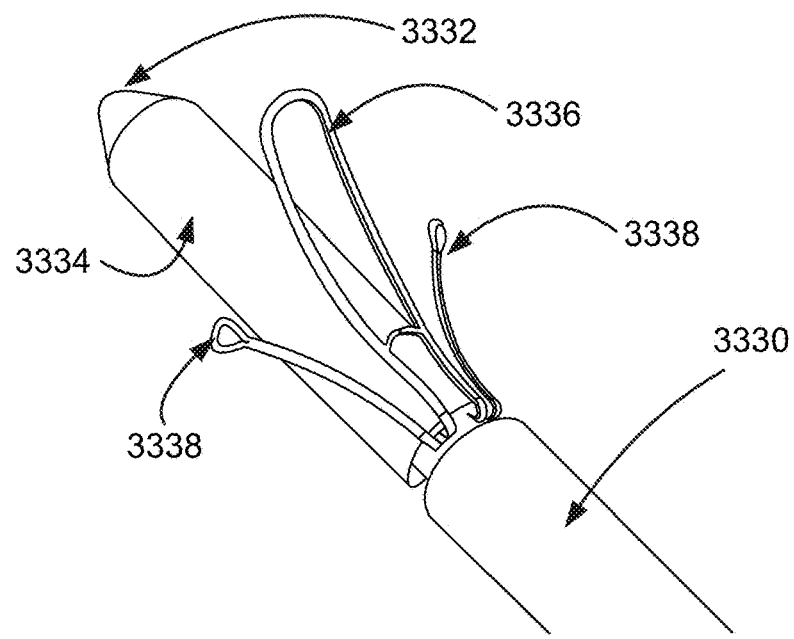
FIGS. 3N-3O are a simplified illustration of a process of pushing a cardiac valve support out of an insertion catheter according to another example embodiment of the invention.
Figure 3O:
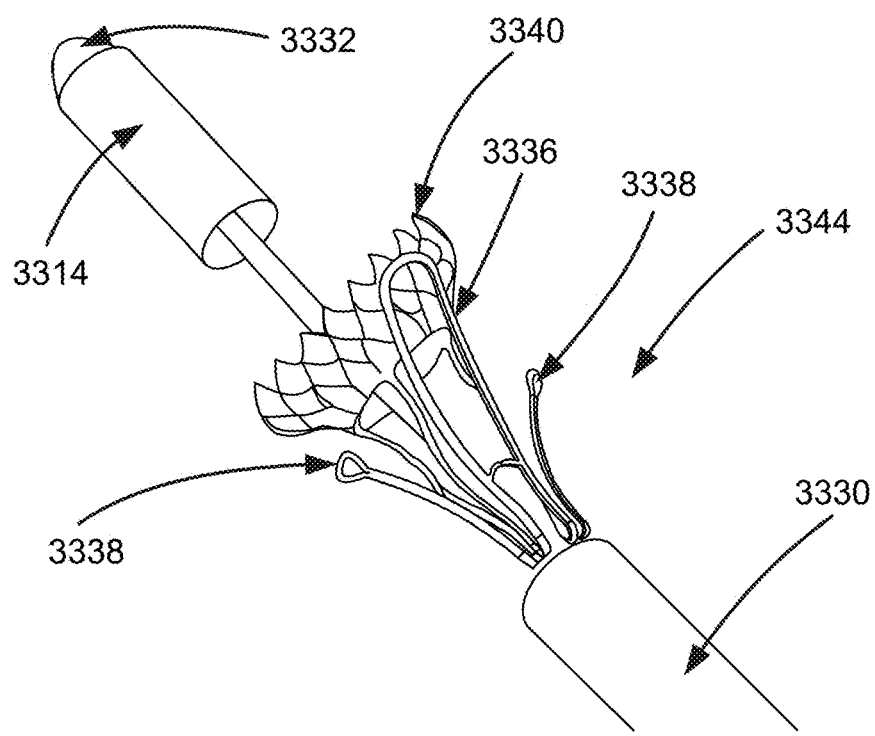
Figure 3P:
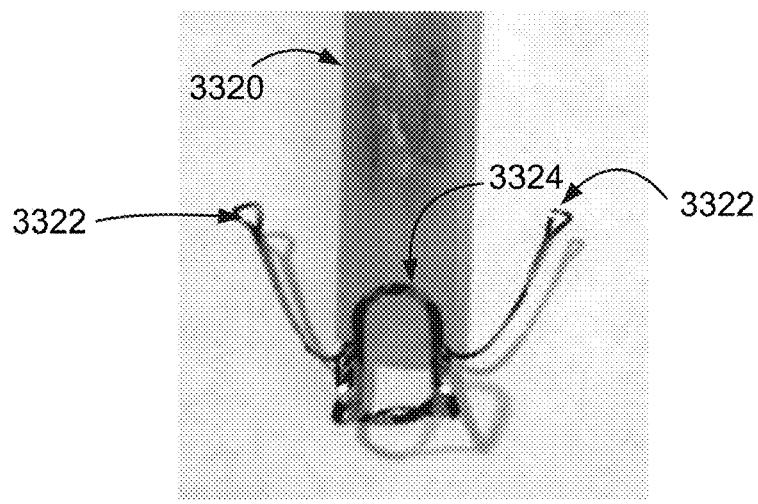
FIG. 3P is an image of components of a cardiac valve support protruding from an insertion catheter according to an example embodiment of the invention.

Reference is now made to FIGS. 3N-3O, which are a simplified illustration of a process of pushing a cardiac valve support out of an insertion catheter according to another example embodiment of the invention.

FIG. 3N depicts a catheter 3330 having a tip 3332 shaped to navigate through blood vessels (lumens). FIG. 3N depicts the tip 3332 having a short sleeve 3334 extended back from the tip 3332. When the catheter 3330 is pulled back relative to the tip 3332 and the sleeve 3334, the catheter 3330 optionally uncovers an anchor extension 3336 and commissure extensions 3338, which optionally expand.

FIG. 3O depicts the catheter 3330, the tip 3332 and the short sleeve 3334. The tip 3332 and the sleeve 3314 have been pushed forward relative to the catheter 3330 and to a cardiac valve support 3344, releasing a frame 3340 of the cardiac valve support 3344 to optionally expand. FIG. 3O also depicts the anchor extension 3336 and the commissure extensions 3338.

In a process of placing the cardiac valve support 3344 the tip 3332 and the sleeve 3314 are pulled back through the center of the cardiac valve support 3344, releasing the cardiac valve support 3344, similarly to the state depicted in FIG. 3M.

Figure 3Q:
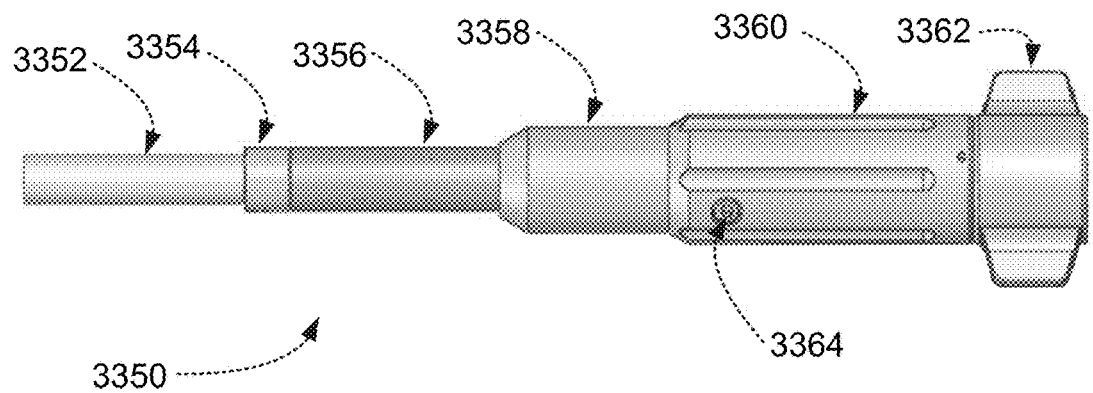
FIGS. 3Q and 3R are simplified illustrations of a side view and a cross sectional view of an example embodiment of a component for inserting a cardiac valve support or a cardiac valve prosthesis according to an example embodiment of the invention.
Figure 3R:
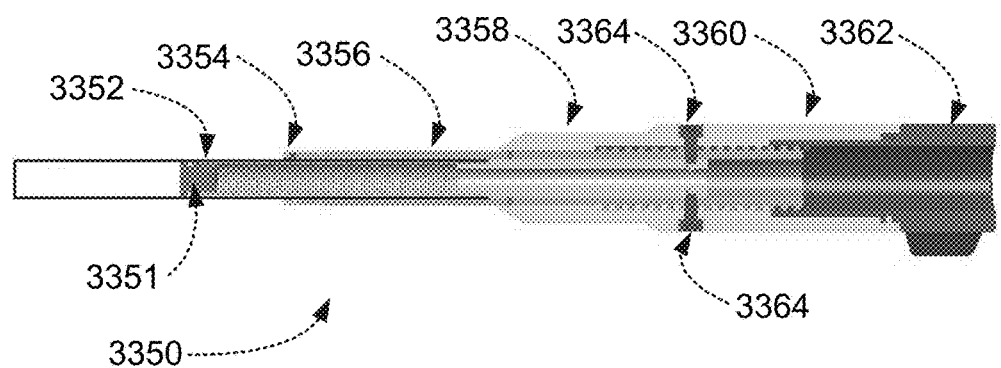

Reference is now made to FIGS. 3Q and 3R, which are simplified illustrations of a side view and a cross sectional view of an example embodiment of a component for inserting a cardiac valve support or a cardiac valve prosthesis according to an example embodiment of the invention.

A device 3350 depicted in FIGS. 3Q and 3R optionally serves to control relative movement of a catheter, tip, and optionally one or more sleeves such as described above with reference to FIGS. 3H-3M and 3N-3O.

FIGS. 3Q and 3R depict:

an inner tube 3352 which optionally serves to encapsulate a cardiac valve support or a cardiac valve prosthesis;

a concentric tube 3356, connected to tube 3352 by a connector 3354, an outer tube 3358, surrounding the concentric tube 3356, and configured to allow the concentric tube 3356 and inner tube 3352 to slide back and forth relative to the outer tube 3358.

In some embodiments the outer tube 3358 optionally has a section 3360 configured for being held by hand.

In some embodiments the device 3350 also includes a section 3362 which can rotate relative to the hand-held section 3360, enabling a potential rotation and/or translation of the concentric tube 3356 and the concentric tube 3352 relative to a section 3351 which is optionally attached to section 3360 by one or more screws 3364.

Figure 4A:
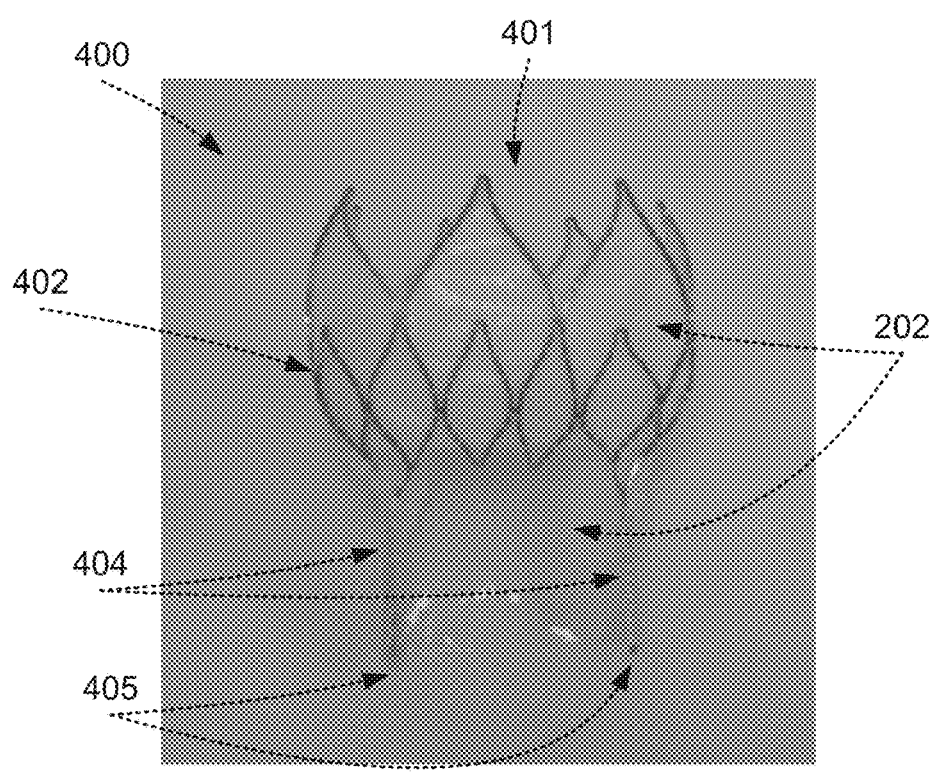
FIG. 4A is a side view image of a cardiac valve prosthesis according to an example embodiment of the invention.

Reference is now made to FIG. 4A, which is a side view image of a cardiac valve prosthesis according to an example embodiment of the invention.

FIG. 4A depicts a device 400, a frame 402, the flexible sheet 202, and a direction of normal flow 401 through the device. The flexible sheet 202 of the example embodiment of FIG. 3A is attached to the frame 402 at many points. In some embodiments the flexible sheet 202 is sewn to the frame 402.

Also depicted are two posts 404, attached to the frame 402. In the example embodiment depicted in FIG. 4A, the two posts are not attached to each other at their downstream ends 405.

Figure 4B:
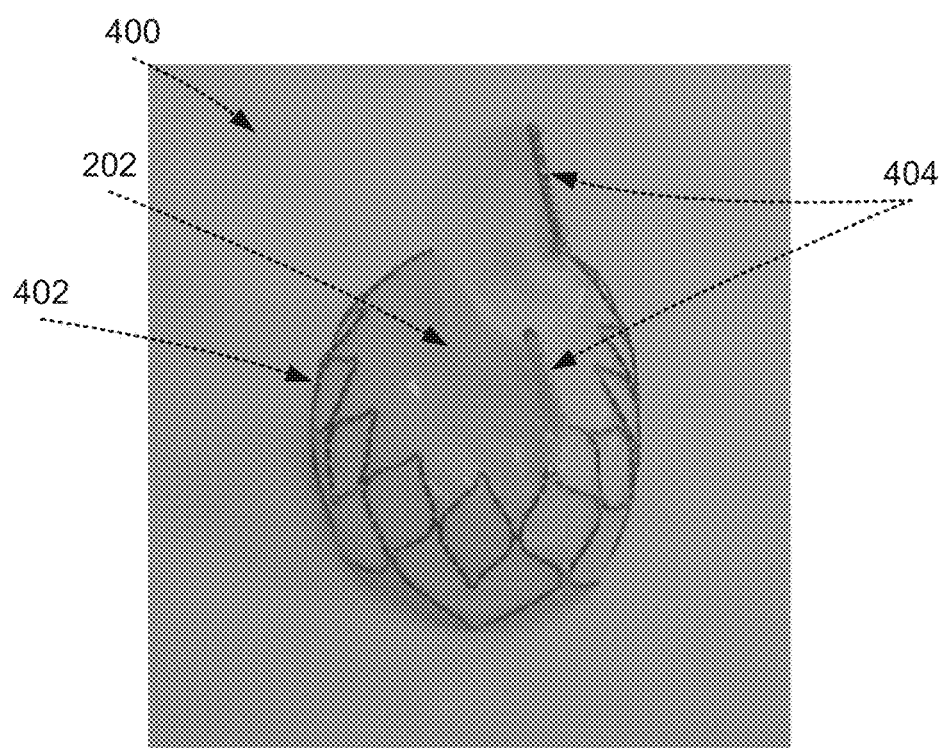
FIG. 4B is a bottom view image of the cardiac valve prosthesis depicted in FIG. 4A.

Reference is now made to FIG. 4B, which is a bottom view image of the cardiac valve prosthesis depicted in FIG. 4A.

FIG. 4B depicts the device 400; the frame 402; the flexible sheet 202; and the posts 404. The direction of normal flow through the device is from the page toward the observer.

FIG. 4B depicts the flexible sheet 202 in a closed position.

In the example embodiment depicted in FIGS. 4A and 4B the posts 404 are on the inside of the flexible sheet 202.

Reference is now made to FIG. 5A, which is a side view image of a cardiac valve support according to an example embodiment of the invention.

FIG. 5A depicts a frame 502, and a direction of normal flow 501 through the device. Also depicted are two posts 504, attached to the frame 502. In the example embodiment depicted in FIG. 5A, the two posts 504 are attached to each other at their downstream end 505.

Also depicted are two anchor extensions 506, attached to the frame 502.

In the example embodiment depicted in FIG. 5A, the two anchor extensions 506 are located at positions which are suitable for extending behind the commissures of the cardiac valve, making the two anchor extensions 506 of FIG. 5A examples of what is termed commissure anchor extensions.

In an exemplary, illustrative configuration, the valve platform of the prosthesis is anchored to a ventricle wall through anchor extensions 506 which pass through commissures of the native valve, or at the plane of the commissures, and may optionally have hooks at their ends which anchor into the ventricular wall below the annulus.

In the example embodiment depicted in FIG. 5A, the two anchor extensions 506 are attached to the frame 502 by virtue of being attached to the posts 504, which are connected to the frame 502. It is noted that in some other example embodiments the two anchor extensions 506 are attached directly to the frame 502.

In the example embodiment depicted in FIG. 5A, the extensions 506 include a support beam 555 whose function is to stiffen the extensions 506 and allow the extensions 506 to resist buckling when pressure is applied.

In some example embodiments, such as an example embodiment of a mitral valve prosthesis, the stiffness is selected so as to resist at least 250 grams of force.

Also depicted is an anchor extension 508, attached to the frame 502. The anchor extension 508 is configured to extend beyond a natural leaflet of the cardiac valve and back behind the leaflet of the cardiac valve, circumventing the leaflet, optionally without interfering with movement of the leaflet, or interfering just a little, potentially preventing the anchor extension and the frame 502 and entire device from shifting back from the downstream side of the annulus of the cardiac valve to the upstream side of the annulus of the cardiac valve. In some embodiments where the anchor extension 508 does interfere with movement of the natural leaflet of the cardiac valve, the prosthesis skirt compensates by nevertheless blocking backward blood flow.

In some embodiments the anchor extension 508 is attached to the frame 502 at one location and extends behind the natural leaflet.

In some embodiments the anchor extension 508 is attached to the frame 502 at a first location, extends behind the natural leaflet, and is attached back to the frame 502 at a second location.

In some embodiments the anchor extension 508 is wrapped with a material (not shown) intended to alleviate a possible rubbing between the anchor extension 508 and the back of the natural leaflet. The material is typically a bio-compatible material. Some examples of material used in example embodiments are: a bio-compatible animal tissue, Teflon, Silicon, polyurethane, polyester and the like.

In the example embodiment depicted in FIG. 5A, the anchor extension 508 is attached to the frame 502 by virtue of being attached to the posts 504, which are connected to the frame 502. It is noted that in other example embodiments the anchor extension 508 is attached directly to the frame 502.

In some example embodiments, the anchor extension 508 is folded behind the posterior leaflet of the mitral valve.

Reference is now made to FIG. 5B, which is a top view image of the cardiac valve support also depicted in FIG. 5A.

FIG. 5B depicts the frame 502; the posts 504; the anchor extensions 506; and friction resistance hooks 566 used for assisting the device to remain in place, for example while deployment of the device is performed, and the anchor extension 508. The direction of normal flow through the device is from the observer into the page.

In some embodiments the anchor extensions 506 are commissure anchor extensions, intended to pass through commissures of the cardiac valve leaflets. When seen from above, such as the depiction of the anchor extensions 506 in FIG. 5B, the anchor extensions 506 are not necessarily at 180-degree opposite sides of the frame 502. The anchor extensions 506 are designed to pass through the commissures of the cardiac valve, and form an angle similar to that existing between the commissures in the cardiac valve. The angle typically lies in a range from 90-120 degrees, or even 70-160 degrees.

An optional use for the friction resistance hooks 566 is to assist the device to remain in place, for example while deployment of the device is performed.

Figure 6:
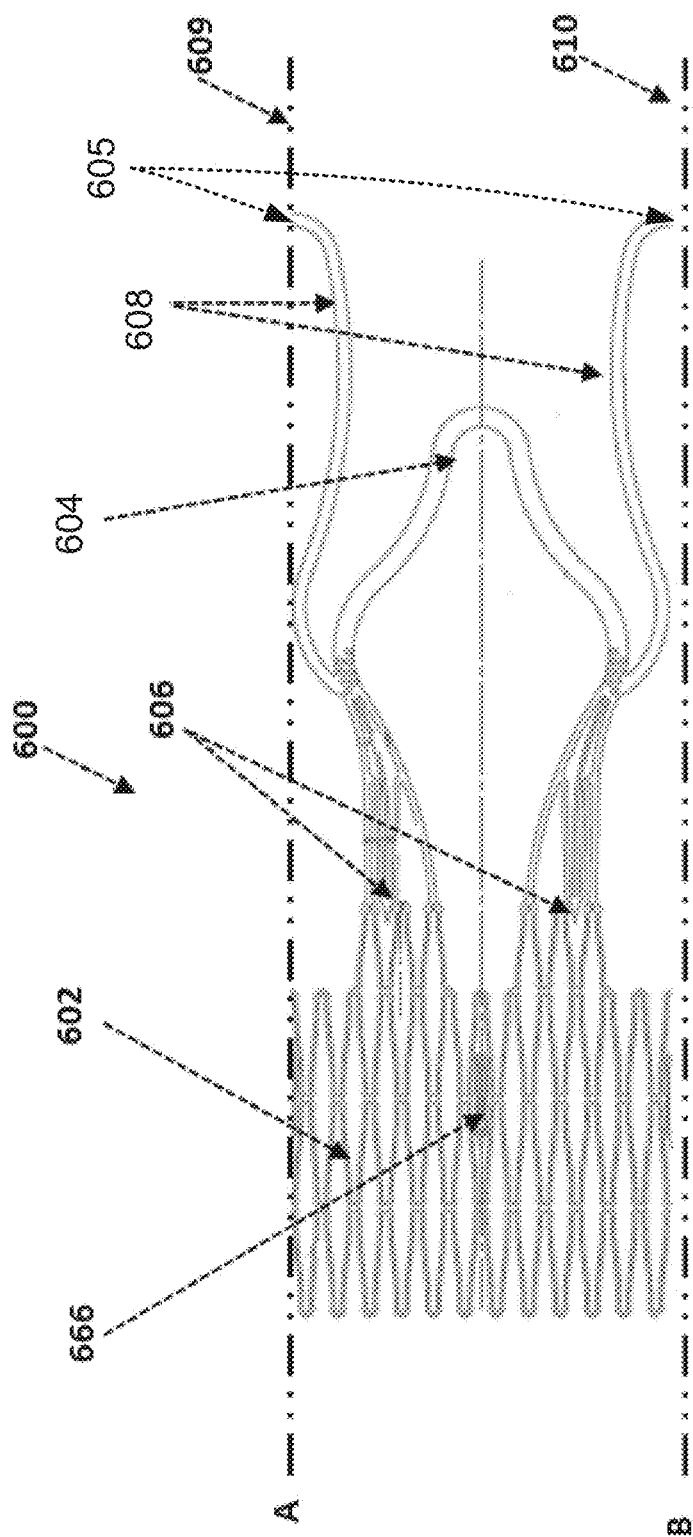
FIG. 6 is a simplified drawing of a cardiac valve support according to an example embodiment of the invention.

Reference is now made to FIG. 6, which is a simplified drawing of a cardiac valve support according to an example embodiment of the invention.

FIG. 6 is a drawing of the example embodiment laid out in a plane, while the example embodiment is a tube. The top construction line A-A 609 of a device 600 depicted in FIG. 6 is actually connected to, and overlaps, the bottom construction line B-B 610 of the device 600 of the device depicted in FIG. 6.

FIG. 6 depicts a frame 602; a post 604; anchor extensions 606; an anchor extension 608; and a friction resistance hook 666 similar to the frame 502; posts 504; anchor extension 508, friction resistance hooks 566, and anchor extensions 506 of FIGS. 5A and 5B.

The direction of normal flow through the device 600 is from left to right.

The anchor extension 608 is connected to itself at its tip 605, which is depicted on both of the overlapping construction lines A-A 609 and B-B 610.

Figure 7A:
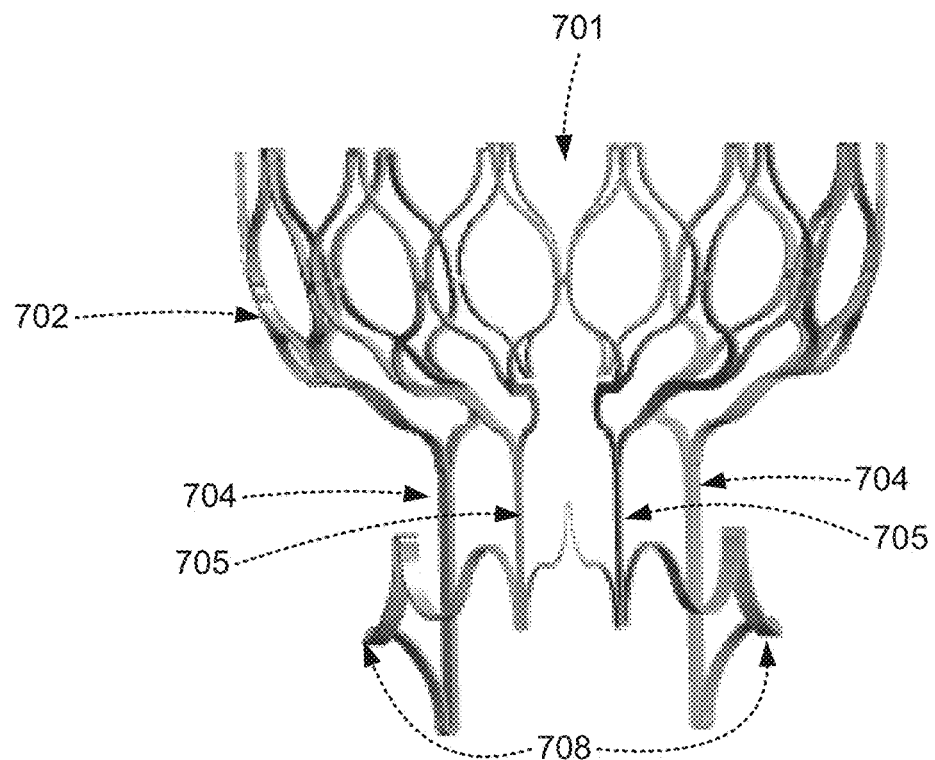
FIG. 7A is a front view image of a cardiac valve support according to an example embodiment of the invention.

Reference is now made to FIG. 7A, which is a front view image of a cardiac valve support according to an example embodiment of the invention.

FIG. 7A depicts a frame 702, and a direction of normal flow 701 through the device. Also depicted are two posts 704, and additional posts 705 attached to the frame 702. In the example embodiment depicted in FIG. 7A, the two posts 704 are attached to each other differently than, for example the posts of FIGS. 3A and 5A.

FIG. 7A depicts posts 704 and extensions 705, attached to the frame 702. The extension 708 in the embodiment depicted in FIGS. 7A and 7B optionally serve to resist a potential collapse motion of the two posts 704 inwardly towards a center of the lumen of the valve, which might allow an inversion of the leaflets (not shown) of the device upstream.

Figure 7B:
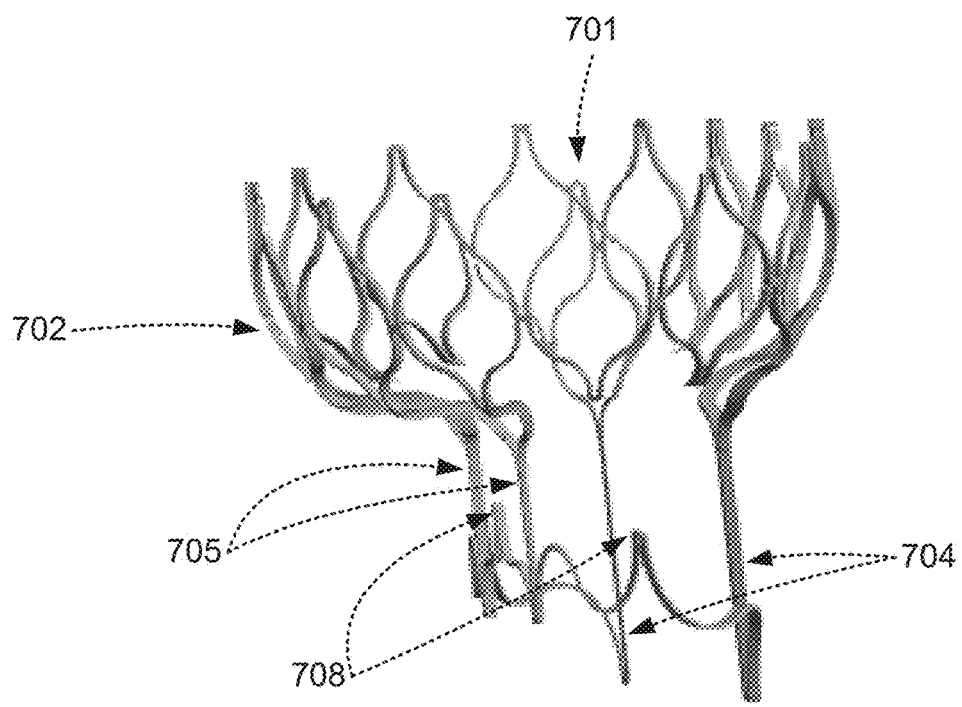
FIG. 7B is a side view image of a cardiac valve support according to the example embodiment of the invention also depicted in FIG. 7A.

The extension 708 is also supported by the extensions 705 which are, in the example embodiment of FIGS. 7A and 7B, connected to the frame 702.

In some embodiments, the extensions 708, and the additional posts 705 are configured to lie in the curved plane of coaptation of the two natural leaflets, and as such, to minimize and even eliminate affecting the natural movement of the natural leaflets.

In the example embodiment of FIG. 7A, the extension 708 connects the tips of the posts 704.

In the example embodiment depicted in FIG. 7A, the extension 708 is attached to the frame 702 by virtue of being attached to the posts 704, and the additional posts 705, which are connected to the frame 702.

Reference is now made to FIG. 7B, which is a side view image of a cardiac valve support according to the example embodiment of the invention also depicted in FIG. 7A.

FIG. 7B depicts the frame 702; the posts 704; and additional posts 705; and the extension 708. The direction of normal flow 701 through the device is also depicted.

Figure 8A:
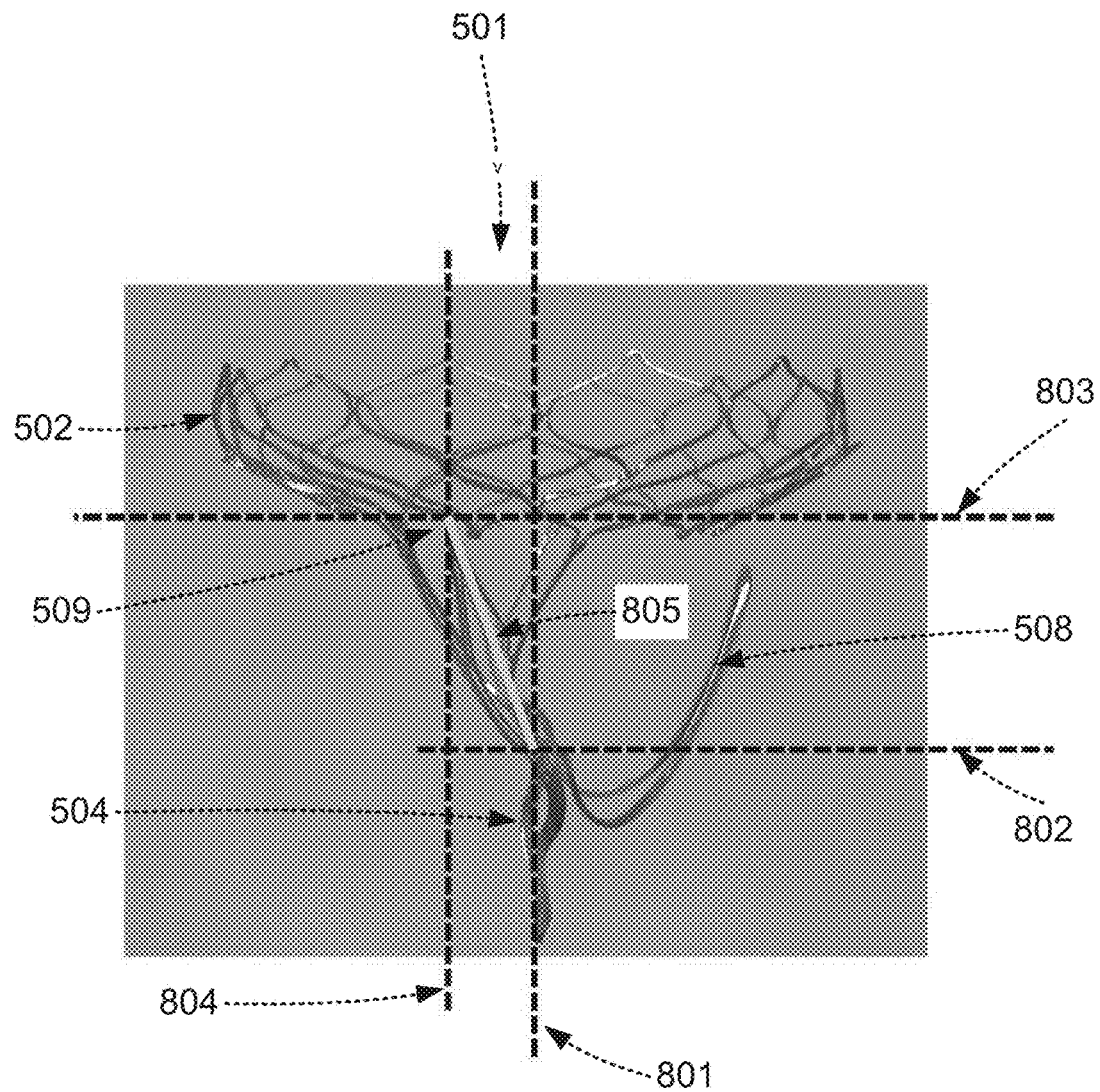
FIG. 8A is a side view image of a cardiac valve support according to the example embodiment of the invention also depicted in FIGS. 5A and 5B.

Reference is now made to FIG. 8A, which is a side view image of a cardiac valve support according to the example embodiment of the invention also depicted in FIGS. 5A and 5B.

FIG. 8A depicts the frame 502, and the direction of normal flow 501 through the device. Also depicted are the two posts 504, which in the side view of FIG. 8A are one behind the other and seen as one.

Also depicted is the anchor extension 508, attached to the posts 504, which are connected to the frame 502. The anchor extension 508 is configured to extend beyond a leaflet of the cardiac valve and back behind the leaflet of the cardiac valve, circumventing the leaflet, optionally without interfering with movement of the leaflet, potentially preventing the anchor extension and the frame 502 and entire device from shifting back from the downstream side of the annulus of the cardiac valve to the upstream side of the annulus of the cardiac valve.

FIG. 8A depicts four construction lines 801 802 803 804 overlaid on top of the device depicted in FIG. 8A.

The first construction line 801 is approximately parallel to the direction of blood flow 501 through the device, at approximately the centerline of the valve annulus. It may be seen that in the example embodiment of FIG. 8A the posts 504 are parallel to the direction of flow 501, and it is noted that they do not need to be so in all embodiments.

The second construction 802 depicts a plane representing the free edge of the natural leaflets.

The third line 803 line depicts a plane corresponding to the plane of the natural annulus and is approximately perpendicular to the direction of flow 501.

The fourth construction line 804 depicts the offset of a point 509 where the commissure anchors 506 of FIGS. 5A and 5B are located relative to the first construction line 801.

A line 805, connecting the point 509 of coincidence of lines 803 and 804 and the point of coincidence of lines 801 and 802, depicts an angle representing a general tilt of the posts 504.

In some embodiments, the prosthesis device is built so that the angle between lines 803 and 805 is such which does not have the artificial leaflets (not shown) force the heart's natural leaflets (not shown) outward to where they might interfere with blood flow. In some embodiments the angle between lines 803 and 805 is, by way of a non-limiting example, in the range between 50 and 85 degrees.

For example, in a case where the device of FIG. 8A is implanted to assist operation of a mitral valve, the angle is selected so as not to push the leaflets to where they might interfere with the Left Ventricle Outflow Track (LVOT).

In some embodiments, the posts 504 are designed at an angle away from a neighboring aortic valve, preventing blood flow obstruction through the Left Ventricle Outflow Track (LVOT).

A potential advantage of some embodiments of the invention is that by allowing a natural anterior leaflet to function, the native anterior leaflet moves away from the LVOT, or the neighboring aortic valve, during systole, thus preventing the native leaflet from obstructing flow through the aortic valve.

In some embodiments, the prosthesis of the example embodiment depicted in FIG. 8A is designed to assist the natural heart valve and not to disturb its natural movement. In such embodiments, the posts 504 pass through or near the natural commissures, which are located at the intersection of a construction line 803 located at the plane of the natural heart valve annulus, and a construction line 804 which is offset from the construction line 801 of the centerline of the natural valve annulus. In such embodiments, a coaptation line at a downstream side (e.g. ventricular side) of the prosthesis preferably starts at or near a center plane of the natural heart valve, depicted by the construction line 801, and also perpendicular to the plane of the drawing.

Locating the coaptation line as described potentially increases efficiency and durability of the prosthesis leaflets, by equalizing stresses on the two prosthesis leaflets. The configuration of FIG. 8A is believed to optimize prosthesis valve durability as well as minimize disturbance to the natural valve leaflets.

The embodiment depicted in FIG. 8A has a curved and/or angled post design along a line depicted in FIG. 8A as construction line 805 which starts at a location corresponding to the natural commissures 509 and ends at an intersection of construction line 802 and construction line 801.

It is noted that in some embodiments more than two artificial leaflets are included in the prosthesis, and possibly more than two posts.

By way of one non-limiting example embodiment, a prosthesis for the tricuspid valve, which has three natural leaflets, optionally includes three artificial leaflets generally corresponding to the three natural leaflets, and optionally includes three posts located where the three natural leaflets meet each other and the side of the tricuspid valve.

By way of another non-limiting example embodiment, a prosthesis for the tricuspid valve, which has three natural leaflets, optionally includes only two artificial leaflets.

Figure 8B:
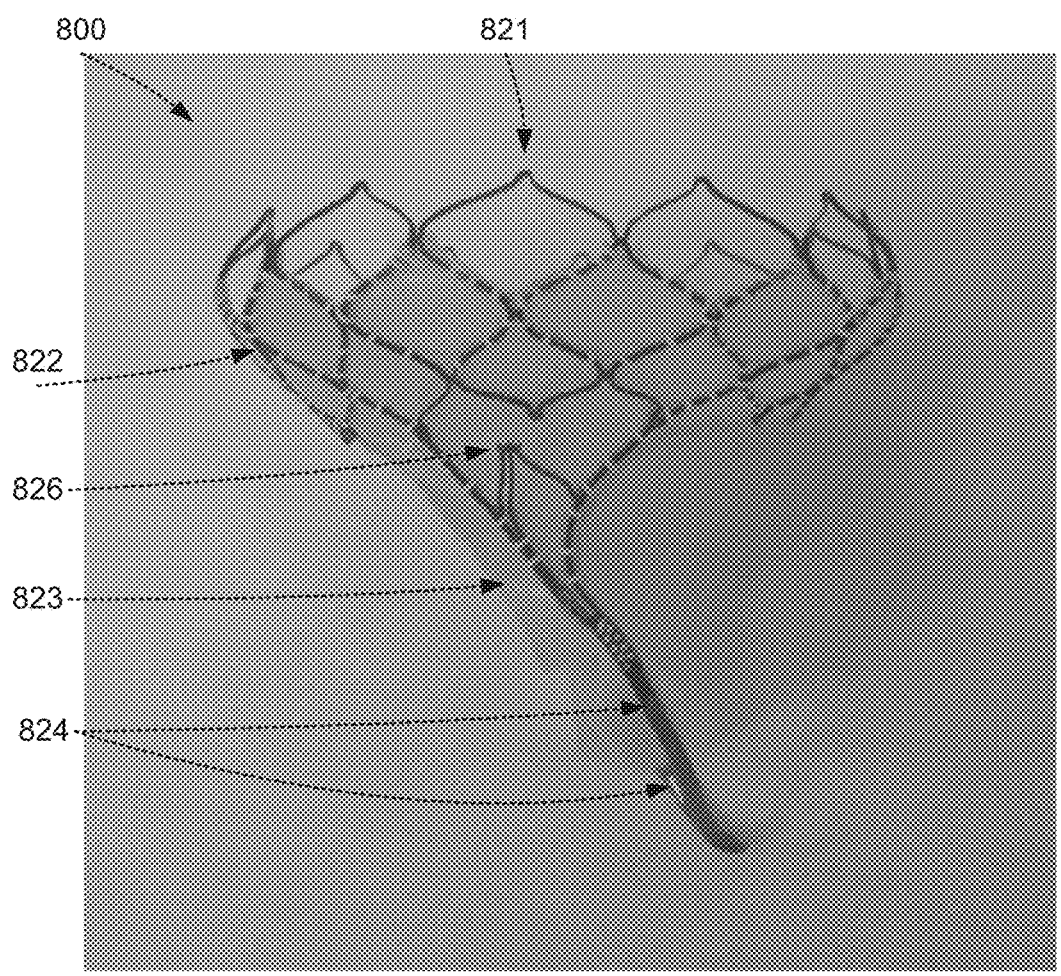
FIG. 8B is a side view image of a cardiac valve prosthesis according to an example embodiment of the invention.

Reference is now made to FIG. 8B, which is a side view image of a cardiac valve prosthesis according to an example embodiment of the invention.

FIG. 8B depicts a device 800, including a frame 822, a flexible sheet 823, and a direction of normal flow 821 through the device. Also depicted are two posts 824. One of the two posts 824 is clearly visible in front of the flexible sheet 823, while the other one of the two posts 824 is visible at the bottom, where the flexible sheet 823 does not reach.

Also depicted is one of two commissure anchor extensions 826, attached to the frame 822 at a base of the posts 824.

The two posts 824, are configured at an angle so as not to force the heart's natural leaflets (not shown) outward to where they might interfere with blood flow.

For example, in a case where the device of FIG. 8B is implanted to assist operation of a mitral valve, the angle of the posts 824 is selected so as not to push the leaflets to where they might interfere with the Left Ventricle Outflow Track (LVOT).

For example, in a case where the device of FIG. 8B is implanted to assist operation of a mitral valve, the shape of the flexible sheet 823 is selected so as not to be collapsible to an extent that might push the leaflets to where they might interfere with the Left Ventricle Outflow Track (LVOT).

Some example dimensions of example embodiments of the prosthesis device are:

A coaptation height of flexible sheet (e.g. sheet 202 of FIGS. 2A-2C) is preferably between approximately 3 and 6 mm or more.

A length of the skirt, or sheet 202, is optionally in a range of approximately 2-7 mm longer than the length of the native leaflets.

A shape of the skirt, or sheet 202, optionally conforms to the angle of the frame.

Figure 8C:
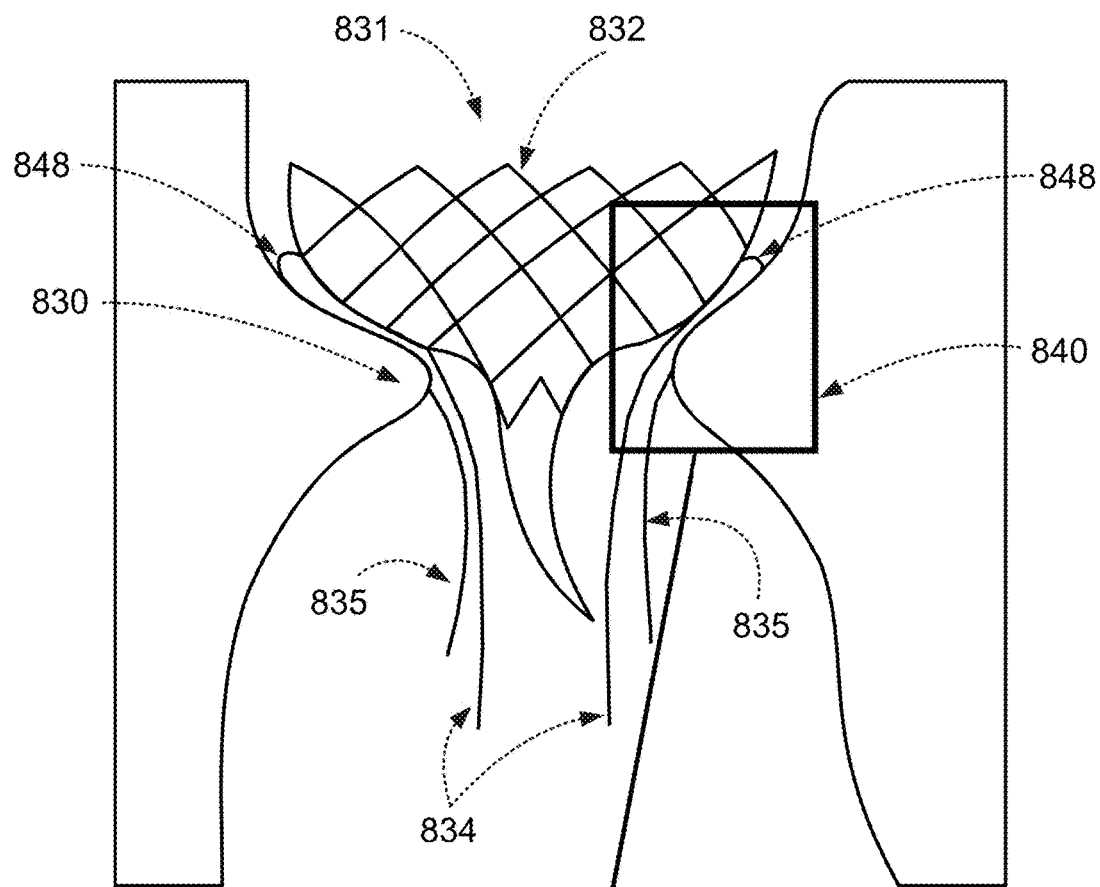
FIG. 8C is a simplified illustration of a cardiac valve prosthesis according to yet another example embodiment of the invention.
Figure 8C:
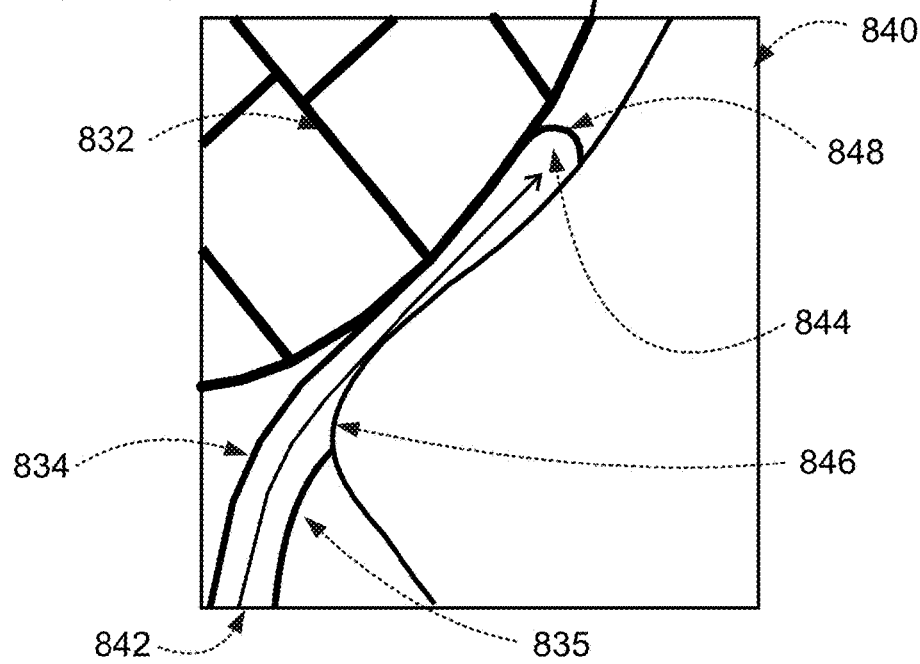

Reference is now made to FIG. 8C, which is a simplified illustration of a cardiac valve prosthesis according to yet another example embodiment of the invention.

FIG. 8C depicts a prosthetic device 831, in place in a cardiac valve. In the example embodiment of FIG. 8C, the prosthetic device 831 is depicted in the mitral valve 830. Some of the components of the prosthetic device 831 are depicted in FIG. 8C, such as a frame 832 and prosthetic leaflets 834 located over the native leaflets 835 of the mitral valve 830.

An enlarged drawing 840 of a section of the illustration of FIG. 8C depicts the frame 832 of the prosthetic device 831, a native leaflet 835 of the mitral valve 830, and a prosthetic leaflet 834.

The example embodiment of FIG. 8C depicts a solution to a possible problem. If blood 842 should attempt to flow upstream, between the native leaflet 835 and the prosthetic leaflet 834, a seal 844 is attached to an outside of the prosthetic device 831, so as to seal a possible gap between the prosthetic device 831 and walls of the atrium and/or of the annulus 846 (the example embodiment of a seal at the annulus 846 is not depicted in FIG. 8C).

In some embodiments, the seal 844 is attached to the prosthetic device 831 by extensions attached to the frame 832, termed herein seal extensions 848.

In some embodiments the seal extensions 848 hold a seal 844 around an outer circumference of the prosthesis which will prevent blood 842 from passing into the atrium. The seal may be constructed of pericardium tissue, or of some biocompatible synthetic material such as polyester, etc.

In some embodiments, the seal 844 is supported by seal extensions 848 supported by frame extensions attached to the frame 832 and/or by part of the frame 832.

In some embodiments, the frame extensions 848 are made of Nitinol.

Figure 8D:
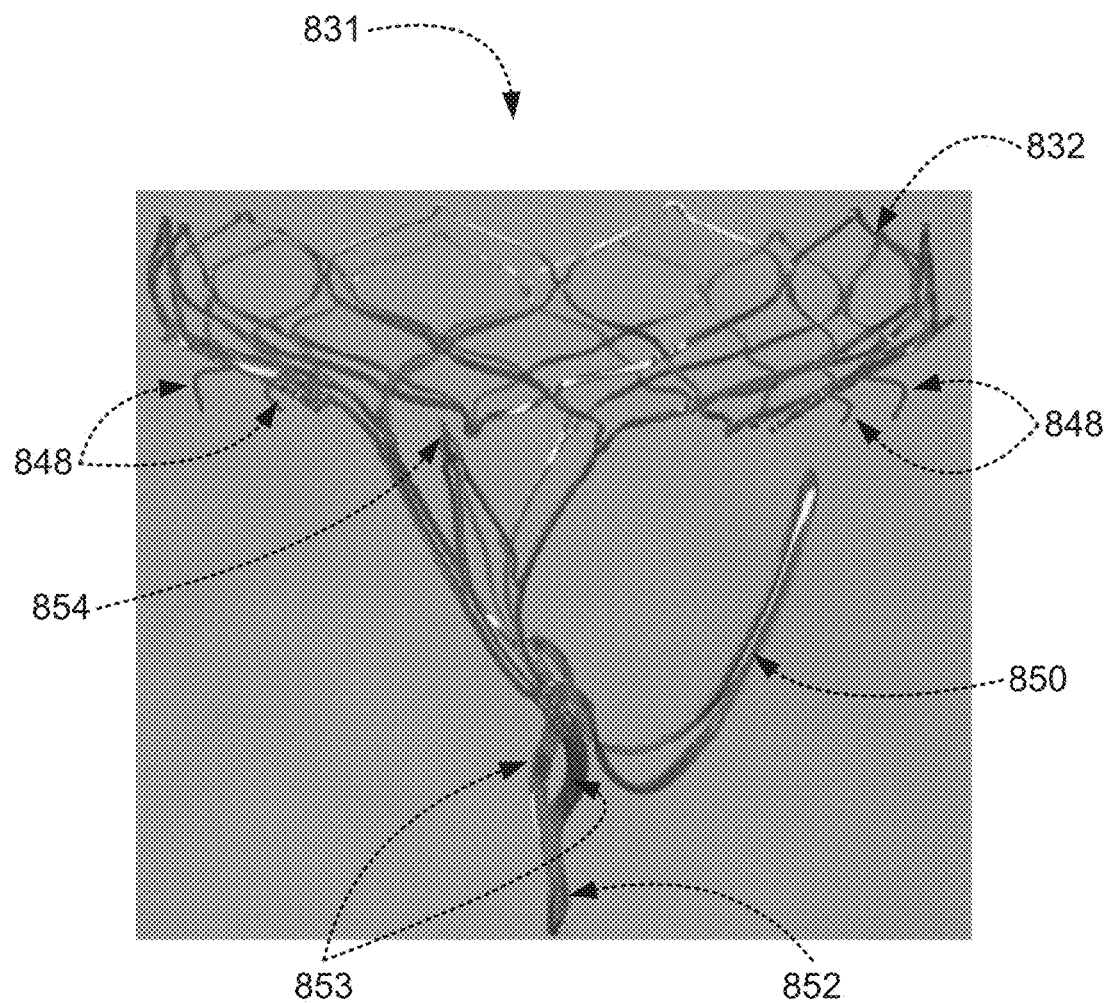
FIG. 8D is an image of part of a cardiac valve support also described with reference to FIG. 8C.

Reference is now made to FIG. 8D, which is an image of part of a cardiac valve support also described with reference to FIG. 8C.

FIG. 8D depicts the frame 832 and some of the frame extensions of the prosthetic device 831 of FIG. 8C. Visible in FIG. 8D are the frame 832, the seal extensions 848, an anchor extension 854 (similar to the anchor extension 506 of FIG. 5A), an anchor extension 850 (similar to the anchor extension 508 of FIG. 5A), and posts 853 connected at their tips 852, (similar to the two posts 504 of FIG. 5A, which are attached to each other at their downstream end 505).

Figure 8E:
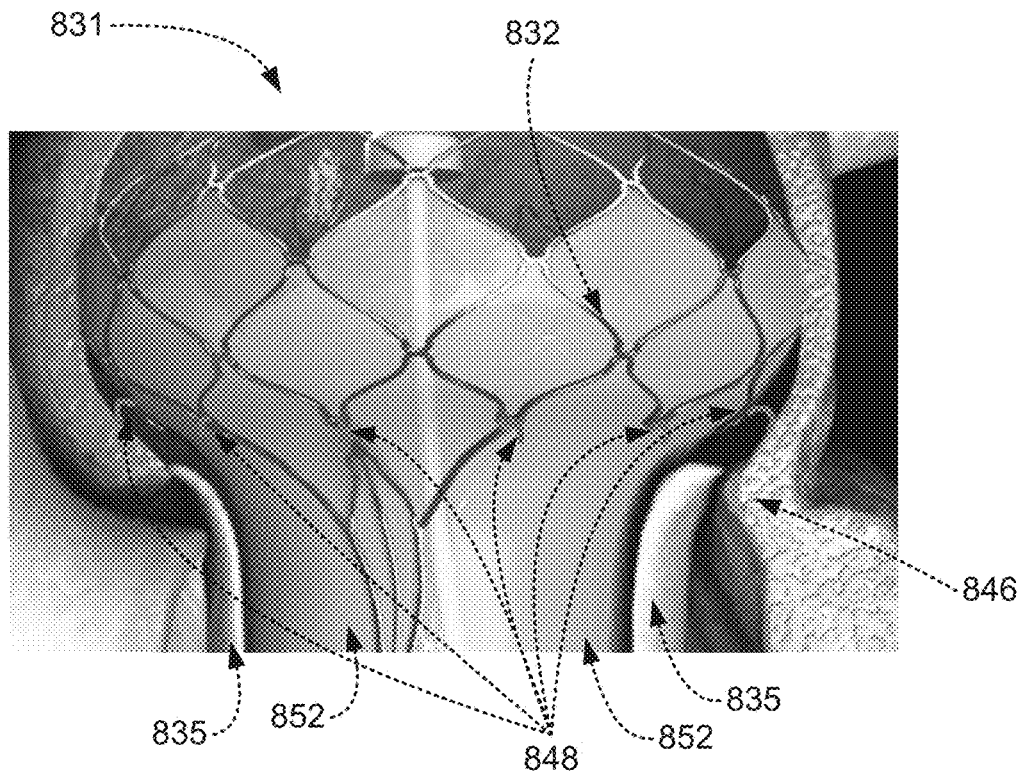
FIG. 8E is a simplified illustration of part of a cardiac valve prosthesis also described with reference to FIG. 8C.

Reference is now made to FIG. 8E, which is a simplified illustration of part of a cardiac valve prosthesis also described with reference to FIG. 8C.

FIG. 8E depicts part of the prosthetic device 831 in place in a mitral valve of a heart, showing also the natural valve leaflets 835.

FIG. 8E depicts the frame 832 and some of the frame extensions of the prosthetic device 831 of FIG. 8C. Visible in FIG. 8E are the frame 832, the seal extensions 848, and a prosthetic leaflet 852 or skirt.

Figure 8F:
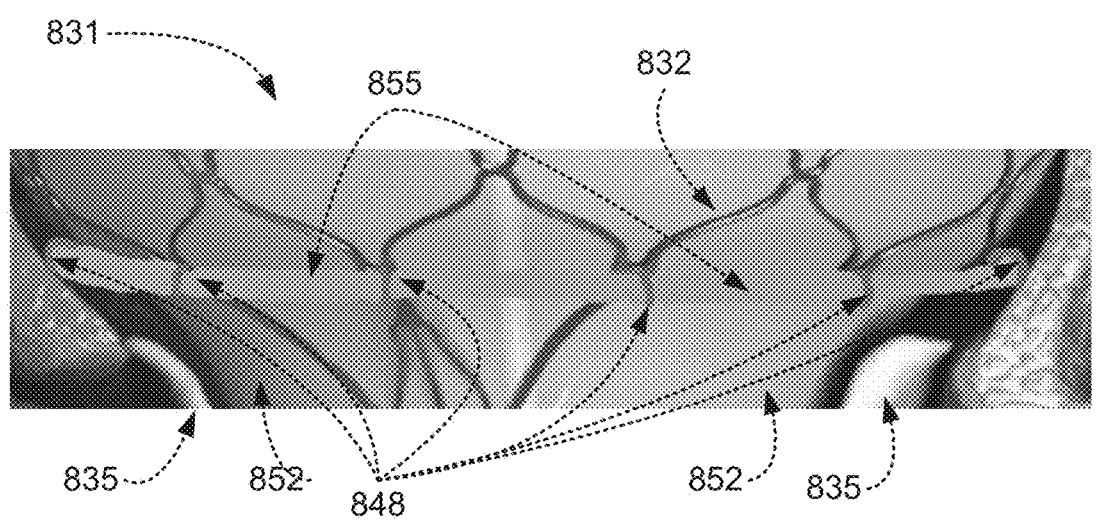
FIG. 8F is a simplified illustration of part of the cardiac valve prosthesis also described with reference to FIG. 8C, showing a seal.

Reference is now made to FIG. 8F, which is a simplified illustration of part of the cardiac valve prosthesis also described with reference to FIG. 8C, showing a seal ring 855.

FIG. 8F depicts part of the prosthetic device 831 in place in a mitral valve of a heart, showing also the natural valve leaflets 835.

FIG. 8F depicts the frame 832, some of the frame extensions of the prosthetic device 831 of FIG. 8C, and the seal 854 of the prosthetic device 831. Visible in FIG. 8F are the seal extensions 848, and a prosthetic leaflet 852 or skirt. The seal 854 is held in place by the seal extensions 848.

Figure 8G:
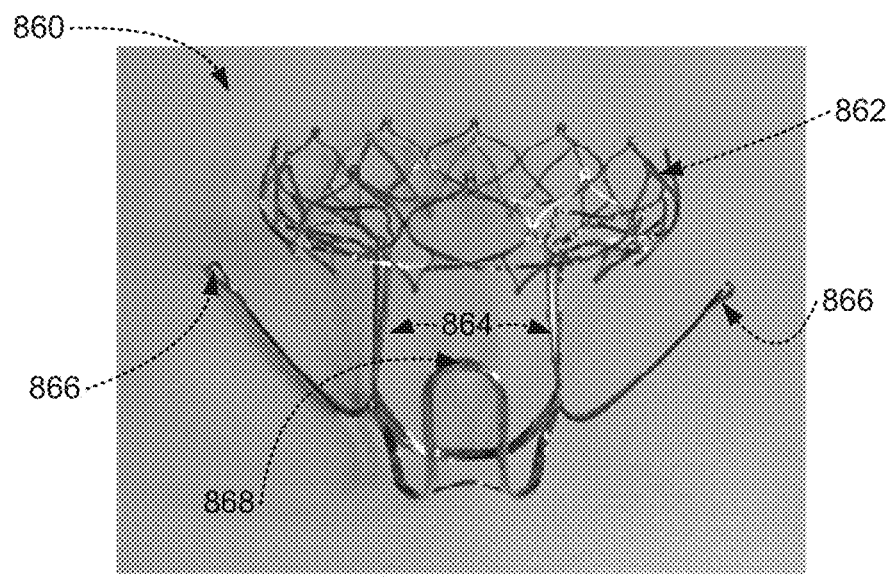
FIG. 8G is an image of a cardiac valve support according to an example embodiment of the invention.

Reference is now made to FIG. 8G, which is an image of a cardiac valve support 860 according to an example embodiment of the invention.

FIG. 8G depicts the cardiac valve support 860 including a frame 862, posts 864, commissure extensions 866, and an anchor extension 868.

It is noted that in the example embodiments depicted in FIG. 8G the commissure extensions 866 are attached to the posts 864 lower than in the example embodiments depicted in FIG. 3A and in FIG. 5A. The posts 864 are designed to pass approximately through the commissures, and the commissure extensions 866 are designed to pass back up behind the chordea, with no possibility of interfering with the natural leaflets, since they are attached to the posts 864 low enough.

Figure 8H:
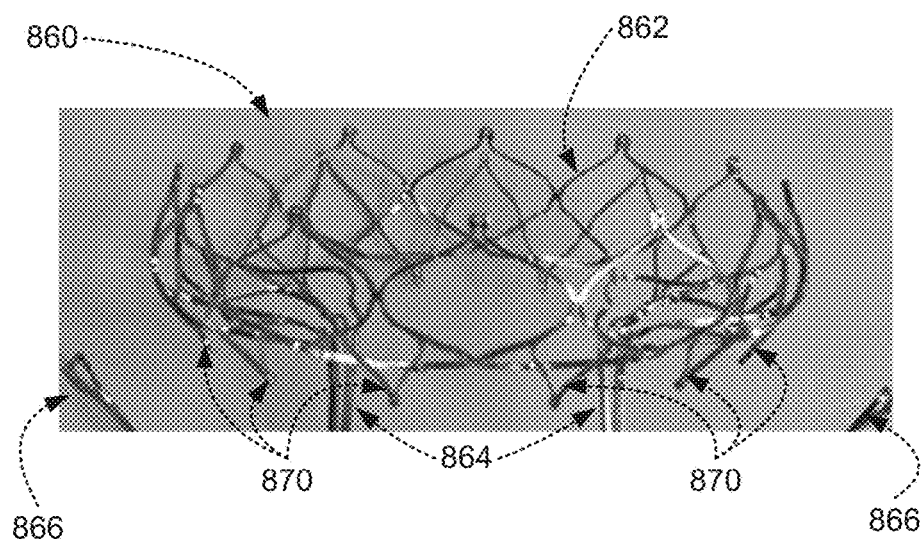
FIG. 8H is an enlarged image of the example embodiment depicted in FIG. 8G.

Reference is now made to FIG. 8H, which is an enlarged image of the example embodiment depicted in FIG. 8G.

FIG. 8H depicts the cardiac valve support 860, the frame 862, the posts 864, and the commissure extensions 866. FIG.

8H also depicts short frame extensions 870 designed to optionally assist in preventing potential leakage around a valve such as the sheet 202 of flexible material depicted in FIGS. 2A-C and 4A-B. The short frame extensions 870 are designed to provide support to seal extensions, such as the seal extensions 848 depicted in FIGS. 8B-C.

Figure 8I:
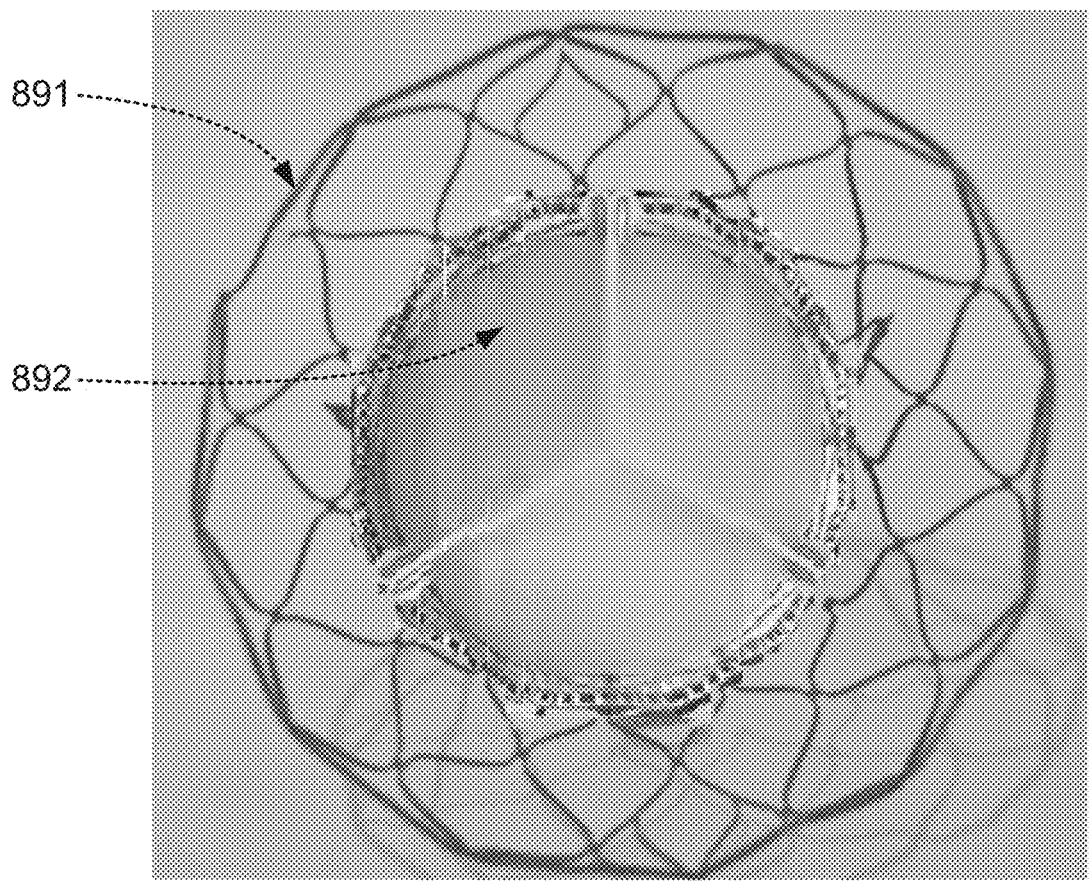
FIG. 8I is an image of a cardiac valve prosthesis placed atop a cardiac valve support according to an example embodiment of the invention.

Reference is now made to FIG. 8I, which is an image of a cardiac valve prosthesis 892 placed atop a cardiac valve support 891 according to an example embodiment of the invention.

FIG. 8I is a top view of a cardiac valve support 891 constructed according to an example embodiment of the invention. In some embodiments, as described herein, the cardiac valve support 891 does not interfere with operation of the natural valve, and so is potentially useful for attaching a cardiac valve prosthesis, such as the cardiac valve prosthesis 892 to the cardiac valve support 891.

FIG. 8I depicts the cardiac valve prosthesis 892 as a tricuspid valve, such as between the right atrium and the right ventricle of a heart.

In some embodiments of the above, the cardiac valve support 891 may be covered with a material such that no blood can enter the atrium form the ventricle around the cardiac valve prosthesis 892.

Figure 8J:
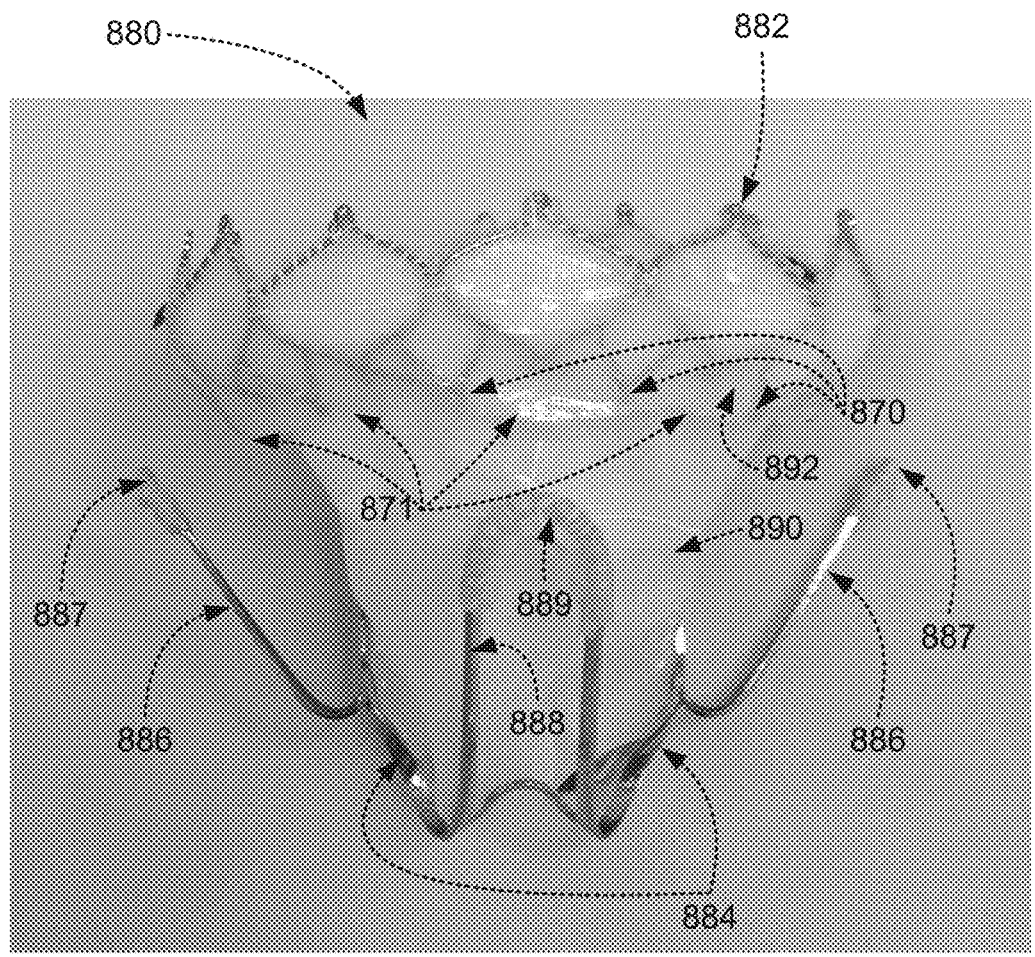
FIG. 8J is an image of a cardiac valve prosthesis according to an example embodiment of the invention.

Reference is now made to FIG. 8J, which is an image of a cardiac valve prosthesis 880 according to an example embodiment of the invention.

FIG. 8J depicts the cardiac valve support 880 including a frame 882; posts 884; commissure extensions 886; an anchor extension 888; a flexible sheet valve 890 similar to the sheet 202 depicted in FIGS. 2A-C and 4A-B; and a seal extension sheet 892 designed to optionally assist in preventing potential leakage around the flexible sheet valve 890. The seal extension sheet 892 is designed to optionally be supported by the short frame extensions 870 described above with reference to FIG. 8J.

In some embodiments a edge 871 of the seal extension sheet 892 is optionally located by the short frame extensions 870. In some embodiments the edge 871 of the seal extension sheet 892 is optionally attached to the short frame extensions 870.

In some embodiments depicted by FIG. 8J the edge 871 of the seal extension sheet 892 is optionally located higher upon the cardiac valve support 880, more toward the frame 882, than the seal ring 855 depicted in FIG. 8F. By locating the seal extension sheet 892 higher upon the cardiac valve support 880 prevention of potential leakage around the seal extension sheet 892 is improved. The seal extension sheet 892 presumably gets support from the frame 882 and/or from the annulus.

In some embodiments tips 887 of the commissure extensions 886 are optionally wrapped by a protective wrapping, optionally a bio-compatible wrapping, so as to prevent a potential rubbing of the tips 887 of the commissure extensions 886 against cardiac tissue.

In some embodiments a tip 889 of the anchor extension 888 is optionally wrapped by a protective wrapping, optionally a bio-compatible wrapping, so as to prevent a potential rubbing of the tip 889 of the anchor extension 888 against cardiac tissue.

Back Pressure on the Assistive Device

Figure 9:
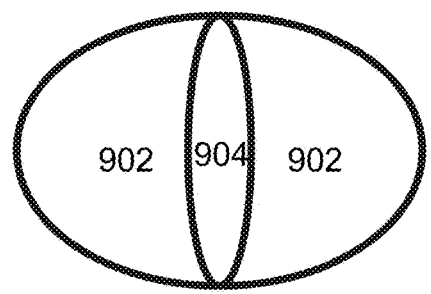
FIG. 9 is a simplified schematic illustration of a top view of a cardiac valve, and a portion of the cardiac valve where problem leaflets may not completely close the cardiac valve.

Reference is now made to FIG. 9, which is a simplified schematic illustration of a top view of a cardiac valve 902, and a portion 904 of the cardiac valve where problem leaflets may not completely close the cardiac valve.

FIG. 9 illustrates how, in a cardiac valve 902 which is problematic and not fully closing, only a portion 904 of the cardiac valve may actually be left open.

In cases of full replacement of the cardiac valve, physicians typically have to attach the replacement valve to the heart in a manner which can withstand systolic pressure of the blood against the full area of the cardiac valve 902.

In embodiments of the invention, the assistive device has to absorb systolic pressure of the blood against the assistive portion 904. A ratio of the force acting on the assistive device, relative to a force acting on a replacement valve, is approximately equal to the ratio of the area of the portion 902 to the area of the entire cardiac valve (area 902/(area 902+area 904)), since the force exerted on the assistive device is approximately equal to the area 902 times the blood pressure, and the force exerted on the replacement valve is equal to the full area of the valve (area 902+area 904) times the blood pressure.

It is noted that, as also mentioned above with reference to FIG. 2C, blood may try to force its way back between the assistive portion 904 and the natural leaflets of the cardiac valve 902. However, the blood back pressure pushes the natural leaflets against the assistive leaflets, blocking its possible backward leakage.

Figure 10:
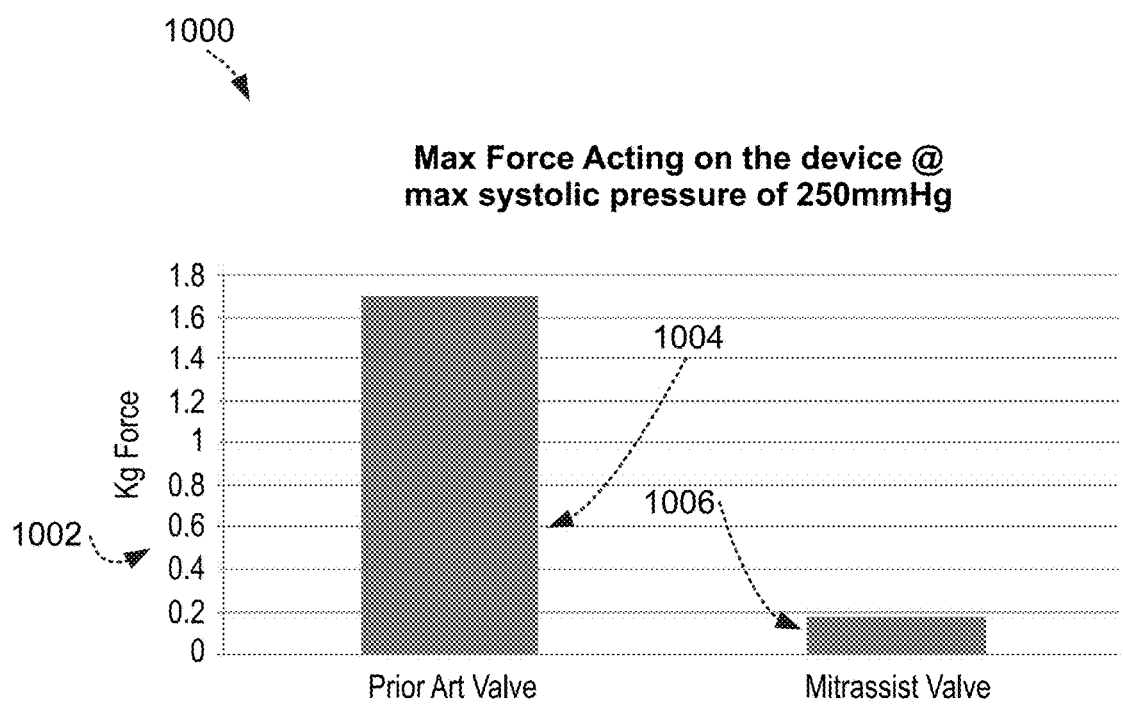
FIG. 10 is a bar graph illustrating force acting on a prior art replacement valve and on an assistive device constructed according to an example embodiment of the invention.

Reference is now made to FIG. 10, which is a bar graph 1000 illustrating force acting on a prior art replacement valve and on a assistive device constructed according to an example embodiment of the invention.

The bar graph 1000 has a y-axis 1002 which corresponds to force exerted, using units of Kg force. The bar graph 1000 depicts a first bar 1004 which illustrates that a prior art valve has approximately 1.7 Kg force exerted upon it under conditions of 250 mm HG maximum systolic pressure, taking an estimated valve area of 5 square centimeters. The bar graph 1000 depicts a second bar 1006 which illustrates that an assistive device constructed according to an example embodiment of the invention has approximately 0.15 Kg force exerted upon it under conditions of 250 mm HG maximum systolic pressure, taking an estimated valve area of 5 square centimeters.

Since the assistive valve feels less force acting backward, the assistive valve enjoys various potential advantages.

A potential advantage is being anchored to withstand lesser forces. The anchors can be smaller. The anchors can potentially be located only at the commissures. The anchors can potentially not be sutured to the heart wall, only being extended behind the commissures.

A potential advantage is including a frame which is lighter and its material optionally thinner than a frame for prior art valves.

A potential advantage is including a frame which is more flexible than a frame for prior art valves.

A potential advantage is including a skirt more flexible than prior art valves.

Figure 11A:
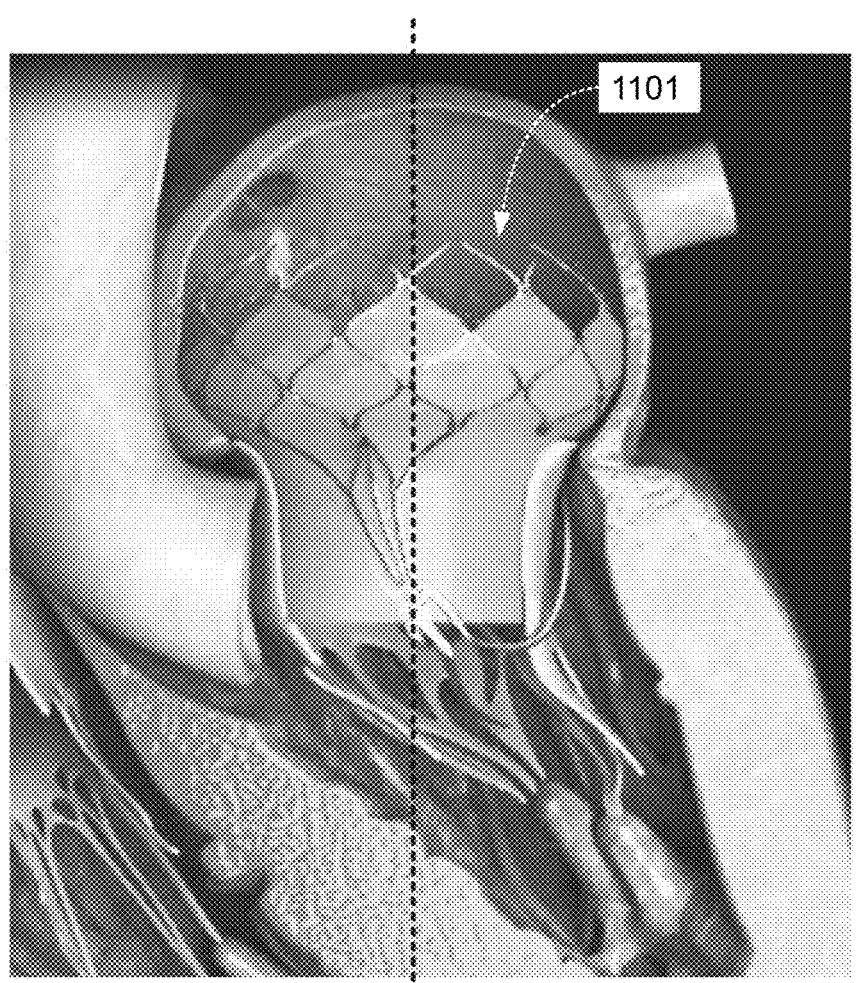
FIG. 11A is a simplified illustration of a cardiac valve prosthesis according to an example embodiment of the invention, placed so as to assist a mitral valve in a heart.

Reference is now made to FIG. 11A, which is a simplified illustration of a cardiac valve prosthesis according to an example embodiment of the invention, placed so as to assist a mitral valve in a heart.

FIG. 11A depicts an assistive prosthesis 1101 and a construction line 1103 which generally passes through a center of the natural mitral valve in a general direction of blood flow.

Figure 11B:
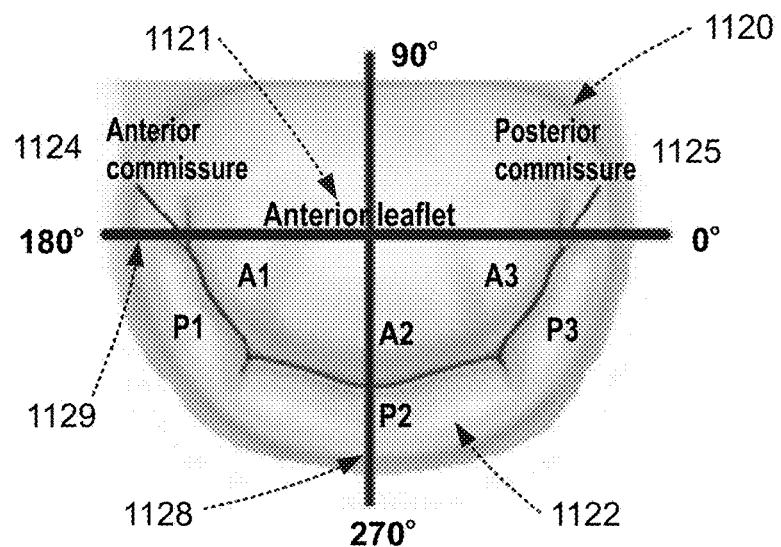
FIG. 11B is a simplified illustration of a top view of a natural mitral valve and an overlay of lines defining an axis system useful in referring to rotations of an implant relative to the natural mitral valve.

Reference is now made to FIG. 11B, which is a simplified illustration of a top view of a natural mitral valve 1120 and an overlay of lines defining an axis system useful in referring to rotations of an implant relative to the natural mitral valve.

FIG. 11B depicts a natural anterior leaflet 1121 and a natural posterior leaflet 1122 of the natural mitral valve 1120. FIG. 11B also depicts the anterior commissure 1124 of the natural mitral valve 1120 and the posterior commissure 1125 of the natural mitral valve 1120.

FIG. 11B also depicts, using an overlay of lines 1128 1129 an axis system useful in referring to rotations of an implant relative to the natural mitral valve. Next to the lines 1128 1129 are written degrees of rotation: 0°, 90°, 180° and 270°.

The first line 1128 is perpendicular to a line which passes through both native valve commissures.

The second line 1129 passes through both native valve commissures.

Figure 12:
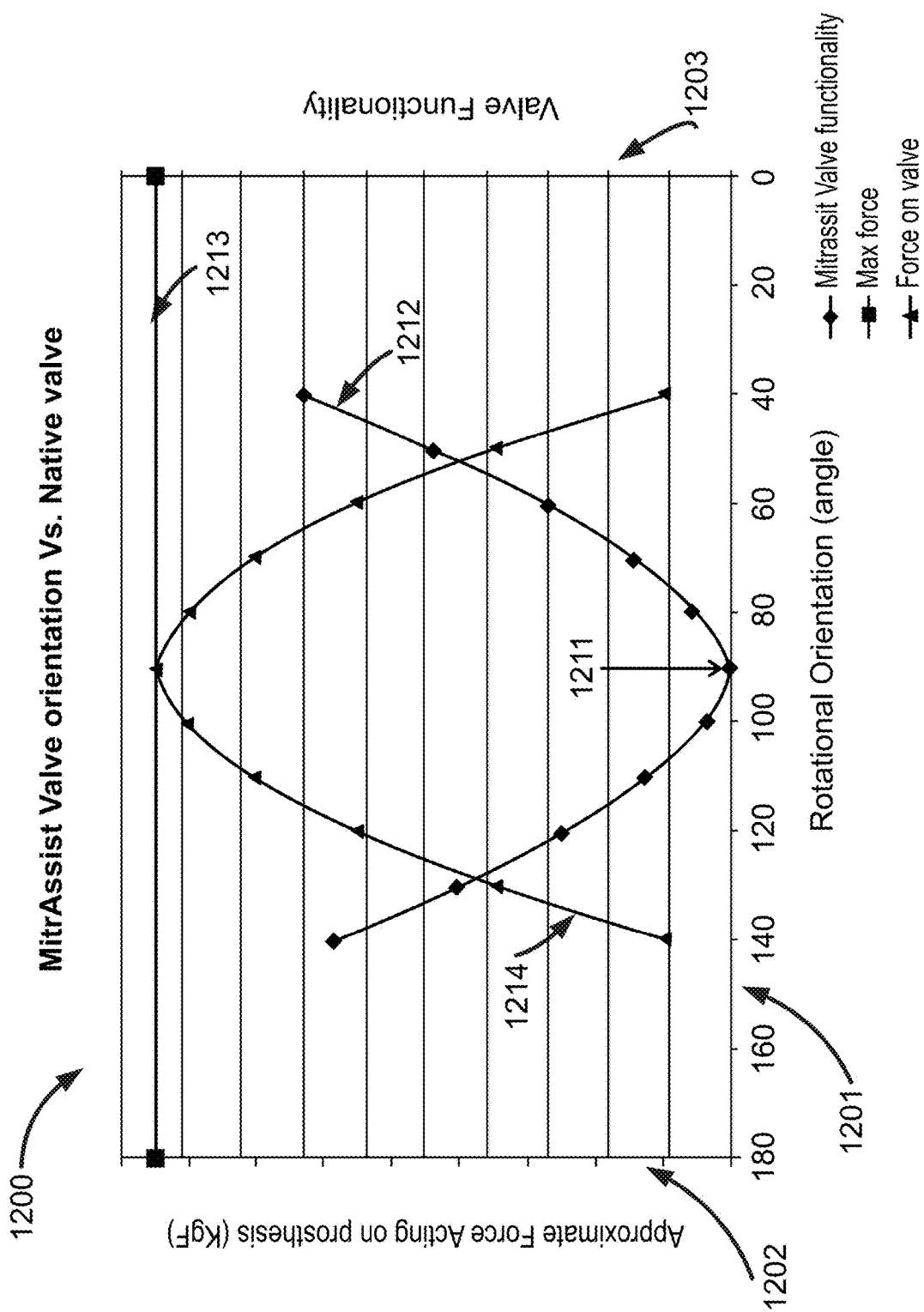
FIG. 12 is a simplified qualitative graph illustrating approximate force and functionality of valves when rotated.

Reference is now made to FIG. 12, which is a simplified qualitative graph 1200 illustrating approximate force and functionality of valves when rotated.

The graph 1200 has an x-axis 1201 representing a degree of rotation of an implant from an arbitrary starting direction.

The graph 1200 has two y-axes 1202 1203.

The left y-axis 1202 represents a qualitative indication corresponding to an approximate force acting on an implant.

The right y-axis 1203 represents a qualitative indication of functionality of a native valve, such as the mitral heart valve, after the assistive or replacement valve is placed over the native heart valve.

The graph 1200 includes three graph lines 1212 1213 1214.

The first graph line 1212 represents qualitatively a degree of natural valve functionality as a function of rotation of an example embodiment of the invention placed in the mitral valve and rotated around an axis corresponding to the construction line 1103 of FIG. 11A.

The first graph line 1212 depicts how the assistive prosthesis preserves native valve functionality, even with suboptimal placement, in contrast to a replacement valve, which destroys native valve functionality, irrespective of positioning.

The second graph line 1213 represents a force acting on a prior art replacement valve, or on a non-assisted healthy mitral valve, which is a constant maximum force since the prior art valve is a replacement valve. An example value for the pressure, given a pressure of 250 mm Hg and area of 5 cm square of a cross section of the mitral valve, is approximately 1.7 Kg force.

The third graph line 1214 represents a force acting on an example embodiment of the invention, for example given a same pressure of 250 mm Hg and area of 5 cm square as used in the second graph line 1213. When the example embodiment prosthesis is placed at 90 degrees with respect to the native valve commissure direction, that of line 1129 of FIG. 11B, native valve functionality is most reduced, and the prosthesis has a maximum force acting upon it.

FIG. 12 also depicts a minimum point 1211 on the first graph line 1212, which is a point at which the example embodiment prosthesis is at a 90 degree rotation, which provides least assistive functionality, and most interfere with the natural valve functionality.

It is noted that the first graph line 1212 is not symmetrical about its minimum point 1211. The first graph line 1212 is higher at a right side of the minimum point 1211, toward its optimal orientation, than at a left side of the minimum point 1211, toward an orientation 180 degrees from the optimal.

If the prosthesis is placed at 180 degrees, most of the native valve functionality is maintained, however, since the two leaflets are not symmetrical, some degree of native valve functionality is damaged.

As used herein the term "about" refers to ±10%.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for placing in a cardiac valve to assist operation of natural cardiac valve leaflets, the device comprising:
   a frame for anchoring the device, comprising a first portion configured to be placed upstream of the cardiac annulus and a second portion configured to be placed downstream of the cardiac annulus, and shaped to prevent the entire frame from shifting downstream of the cardiac valve annulus; and
   at least one anchor extension attached to the frame, the anchor extension configured and circumferentially arranged to extend downstream between the leaflets of the cardiac valve at commissures of the cardiac valve, long enough to extend below an edge of cardiac leaflets, away from a center axis of the frame and back upstream behind the natural leaflets, between the natural leaflet and a ventricle side wall, allowing movement of a natural cardiac leaflet, preventing the anchor extensions from shifting back from the downstream side of the annulus to the upstream side of the annulus.

2. The device of claim 1 in which the anchor extension is configured so as not to interfere with movement of a natural cardiac leaflet.

3. The device of claim 1 in which the anchor extension is configured to extend through the leaflets of the cardiac valve at the commissures of the cardiac valve and below an edge of the natural leaflets and back upstream behind the natural leaflets.

4. The device of claim 1 in which the anchor extension is attached to the frame at a first location, extends behind the natural leaflet, and is attached back to the frame at a second location.

5. The device of claim 1 and further comprising a sheet of flexible material attached to the frame, configured to be placed within the annulus of the cardiac valve, defining a lumen of the sheet extending from an upstream side of the annulus to a downstream side of the annulus; and
   at least two posts attached to the frame, the posts configured to extend along the lumen of the sheet and prevent the lumen from collapsing back from the downstream side of the annulus to the upstream side of the annulus.

6. The device of claim 5 in which ends of the posts are connected at their downstream end.

7. The device of claim 5 in which the cardiac valve is a mitral valve and the posts are attached to the frame at an angle which directs a downstream side of the flexible sheet away from the Left Ventricle Outflow Track (LVOT).

8. The device of claim 5 in which the cardiac valve is a mitral valve and a side of the frame is configured to be at an angle which directs a downstream side of the flexible sheet away from the aortic valve so as not to interfere with the Left Ventricle Outflow Track (LVOT).

9. The device of claim 8 in which the angle is in a range between 50 and 85 degrees.

10. The device of claim 5 in which each one of the posts is curved from a base attached to the frame to a commissure at a coaptation line of the natural cardiac leaflets.

11. The device of claim 5 in which the anchor extensions are attached to the posts.

12. The device of claim 1 and further comprising at least a plurality of seal extensions attached to the frame, the seal extensions configured to attach a seal to an outside circumference of the device, for sealing between the sheet of flexible material and the cardiac valve.

13. The device of claim 12 and further comprising a seal configured for sealing between the sheet of flexible material and the cardiac valve.

14. A device for placing in a cardiac valve to assist operation of the cardiac valve, the device comprising:
   a frame for anchoring the device, comprising a first portion configured to be placed upstream of the cardiac annulus and a second portion configured to be placed downstream of the cardiac annulus, and shaped to prevent the entire frame from shifting downstream of the cardiac valve annulus;
   a sheet of flexible material attached to the frame, configured to be placed within the annulus of the cardiac valve, defining a lumen of the sheet extending from an upstream side of the annulus to a downstream side of the annulus; and
   at least one leaflet anchor extension attached to the frame, the leaflet anchor extension configured to be long enough to extend downstream beyond at least one leaflet of the cardiac valve, away from a center axis of the frame and back upstream behind the leaflet of the cardiac valve, circumventing the leaflet and allowing movement of the leaflet, preventing the anchor extension from shifting back from the downstream side of the annulus to the upstream side of the annulus.

15. The device of claim 14 in which the cardiac valve is a mitral valve and the leaflet anchor extension is attached to the frame and is shaped to extend behind a leaflet of the mitral valve which is distant from the aortic valve.

16. The device of claim 14 and further comprising at least a plurality of seal extensions attached to the frame, the seal extensions configured to attach a seal to an outside circumference of the device, for sealing between the sheet of flexible material and the cardiac valve.

17. The device of claim 16 and further comprising a seal configured for sealing between the sheet of flexible material and the cardiac valve.

18. The device of claim 14 in which the anchor extension is attached to the frame at one end of the anchor extension and is attached back to the frame at a second end of the anchor extension.

19. A method of inserting a prosthesis for placing in a cardiac valve to assist operation of natural cardiac valve leaflets comprising:
   inserting a delivery system which includes a sheath covering the prosthesis into a left atrium from the left ventricle;
   retracting a portion of the sheath until commissure anchors of the prosthesis are at least partially uncovered;
   rotating the delivery system such that commissure anchors are next to corresponding commissures;
   translating the delivery system so as to locate tips of the commissure anchors at the bottom of an annulus of the cardiac valve; and
   retracting the sheath until rest of the prosthesis is uncovered.

20. The method of claim 19 and further comprising, after retracting the sheath until commissure anchors of the prosthesis are uncovered, placing an anchoring extension behind a natural leaflet.

21. A device for placing in a cardiac valve to assist operation of natural cardiac valve leaflets, the device comprising:

- a frame for anchoring the device, comprising a first portion configured to be placed upstream of the cardiac annulus and a second portion configured to be placed downstream of the cardiac annulus, and shaped to prevent the entire frame from shifting downstream of the cardiac valve annulus; and
- at least one anchor extension attached to the frame at a first location, the anchor extension configured and circumferentially arranged to extend downstream between the leaflets of the cardiac valve at commissures of the cardiac valve, long enough to extend below an edge of cardiac leaflets, away from a center axis of the frame and back upstream behind the natural leaflets, between the natural leaflet and a ventricle side wall, and attached back to the frame at a second location, allowing movement of a natural cardiac leaflet, preventing the anchor extensions from shifting back from the downstream side of the annulus to the upstream side of the annulus.

* * * * *